(12) United States Patent
Saji et al.

(10) Patent No.: US 9,950,083 B2
(45) Date of Patent: *Apr. 24, 2018

(54) POLYPEPTIDE AND IMAGING METHOD

(71) Applicants: KYOTO UNIVERSITY, Kyoto (JP); ARKRAY, INC., Kyoto (JP)

(72) Inventors: Hideo Saji, Kyoto (JP); Nobuya Inagaki, Kyoto (JP); Hiroyuki Kimura, Kyoto (JP); Kentaro Toyoda, Kyoto (JP); Hirokazu Matsuda, Kyoto (JP); Mikako Ioroi, Kyoto (JP); Asami Kon, Kyoto (JP)

(73) Assignees: Kyoto University, Kyoto (JP); ARKRAY, Inc., Kyoto (JP)

( * ) Notice: Subject to any disclaimer, the term of this patent is extended or adjusted under 35 U.S.C. 154(b) by 170 days.

This patent is subject to a terminal disclaimer.

(21) Appl. No.: 14/648,467

(22) PCT Filed: Nov. 29, 2013

(86) PCT No.: PCT/JP2013/082249
§ 371 (c)(1),
(2) Date: May 29, 2015

(87) PCT Pub. No.: WO2014/084372
PCT Pub. Date: Jun. 5, 2014

(65) Prior Publication Data
US 2015/0352233 A1    Dec. 10, 2015

(30) Foreign Application Priority Data

Nov. 30, 2012  (JP) ................. 2012-262908

(51) Int. Cl.
| | |
|---|---|
| A61K 49/00 | (2006.01) |
| A61K 51/08 | (2006.01) |
| C07K 14/00 | (2006.01) |
| A61K 49/04 | (2006.01) |
| C07K 14/705 | (2006.01) |
| C07K 14/605 | (2006.01) |
| G01N 33/50 | (2006.01) |
| C07K 1/13 | (2006.01) |
| B82Y 5/00 | (2011.01) |

(52) U.S. Cl.
CPC .......... A61K 51/08 (2013.01); A61K 49/0423 (2013.01); C07K 14/001 (2013.01); C07K 14/605 (2013.01); C07K 14/705 (2013.01); G01N 33/50 (2013.01); B82Y 5/00 (2013.01); C07K 1/13 (2013.01); G01N 2800/042 (2013.01)

(58) Field of Classification Search
CPC ...... A61K 51/00; A61K 51/08; A61K 51/088; A61K 2123/00; A61K 2121/00; A61K 49/00; A61K 49/0423; C07K 14/001; C07K 14/605; C07K 14/705; C07K 1/13; G01N 33/50; G01N 2800/042; B82Y 5/00

USPC .......... 424/1.11, 1.65, 1.69, 1.81, 1.85, 1.89, 424/9.1, 9.2, 9.3, 9.4, 9.5, 9.6; 534/7, 534/10–16; 514/1, 1.1, 20.9, 21.3; 530/300, 308, 324

See application file for complete search history.

(56) References Cited

U.S. PATENT DOCUMENTS

| | | | | |
|---|---|---|---|---|
| 5,679,320 A | * | 10/1997 | Vogel ................ | A61K 49/0002 424/1.69 |
| 8,980,220 B2 | * | 3/2015 | Saji ..................... | A61K 51/088 424/1.69 |
| 8,992,886 B2 | * | 3/2015 | Ahn ..................... | A61K 51/088 424/1.69 |
| 9,278,146 B2 | * | 3/2016 | Saji ..................... | A61K 51/08 |
| 2011/0171129 A1 | | 7/2011 | Inagaki et al. | |
| 2011/0206605 A1 | | 8/2011 | Saji et al. | |

FOREIGN PATENT DOCUMENTS

| | | |
|---|---|---|
| EP | 2510951 A1 | 10/2012 |
| JP | 2005-514444 A | 5/2005 |
| JP | 2011-507863 A | 3/2011 |

(Continued)

OTHER PUBLICATIONS

International Search Report issued in corresponding International Patent Application No. PCT/JP2013/082249 dated Mar. 4, 2014.

(Continued)

*Primary Examiner* — D L Jones
(74) *Attorney, Agent, or Firm* — Morgan, Lewis & Bockius LLP

(57) ABSTRACT

A peptide that can be used as an imaging probe for GLP-1R is provided. In an embodiment, a polypeptide is represented by the following formula (3);

```
                                    (Sequence ID No. 3)
Xaa₁-Leu-Ser-Lys-Gln-Met-Glu-Glu-Glu-Ala-Val-Arg-
Leu-Phe-Ile-Glu-Trp-Leu-Lys-Asn-Gly-Gly-Pro-Ser-
Ser-Gly-Ala-Pro-Pro-Pro-Ser (3)
``` where $Xaa_1$ represents an aspartic acid in which a —Y—X' group binds to an α-amino group, X' includes a chelating site and a radioactive metal nuclide chelated by the chelating site, the chelating site being diethylenetriaminepentaacetic dianhydride (DTPA) or 1,4,7-triazacyclononnane-N,N',N"-triacetic acid (NOTA), and Y represents a linker including a group selected from the group consisting of —$CH_2$—($C_6H_4$)—, —NH—C(=S)—, —NH—($CH_2$)$_5$—C(=O)—, and a combination thereof.

10 Claims, 4 Drawing Sheets

(56) References Cited

FOREIGN PATENT DOCUMENTS

| JP | 4642920 B2 | 3/2011 |
|---|---|---|
| JP | 2011-523697 A | 8/2011 |
| WO | 03/059397 A2 | 7/2003 |
| WO | 2009/079024 A1 | 6/2009 |
| WO | 2009/135015 A2 | 11/2009 |
| WO | 2010/032833 A1 | 3/2010 |
| WO | 2011/068965 A1 | 6/2011 |
| WO | 2011/071083 A1 | 6/2011 |

OTHER PUBLICATIONS

Kambe et al., "Development of 111In-Labeled Exendin-4 Derivative Targeting GLP-1R for Molecular Imaging of Pancreatic beta-Cells," Abstract of the 23rd Symposium on the Role of Metals in Biological Reactions, Biology and Medicine, Jun. 2013.
Extended European Search Report issued in corresponding European Patent Application No. 13858604.5 dated Jun. 9, 2016.
Wild et al., "Lys40(Ahx-DTPA-111In)NH2]Exendin-4, a Very Promising Ligand for Glucagon-like Peptide-1 (GLP-1) Receptor Targeting," Journal of Nuclear Medicine, 47: 2025-2033 (2006).
Office Action issued in corresponding European Patent Application No. 13858604.5 dated Nov. 9, 2017.

\* cited by examiner

SPECT images. INS-1 tumor (arrowheads) and urinary bladder (arrows).
Transverse image; caudal view

POLYPEPTIDE AND IMAGING METHOD

A computer readable text file, entitled "SequenceListing.txt," created on or about May 28, 2015 with a file size of about 21 kb contains the sequence listing for this application and is hereby incorporated by reference in its entirety.

TECHNICAL FIELD

The present disclosure relates to a polypeptide to be used as a labeling precursor, a radiolabeled polypeptide, a composition for imaging, a kit, and use thereof, and an imaging method.

BACKGROUND ART

Glucagon-like peptide-1 (GLP-1) is an important gastrointestinal hormone that has a control function in glucose metabolism, and gastrointestinal secretion and metabolism. GLP-1R is a GLP-1 receptor, which is a seven-transmembrane G protein-coupled receptor.

As a imaging molecular probe that binds to GLP-1R as a target molecule, a peptide, such as GLP-1, Exendin-3, Exendin-4, Exendin(9-39), or a variant thereof that is labeled by labeling molecule is being studied (Patent Document 1, for example).

PRIOR ART DOCUMENTS

Patent Document

[Patent Document 1] Japanese Patent No. 4642920

DISCLOSURE OF INVENTION

Problem to be Solved by the Invention

Attempts have been made to image GLP-1R and/or insulinoma using GLP-1R as a target molecule by utilizing an overexpression of GLP-1R in insulinoma, an expression of GLP-1R in the pancreatic islet cells, and the like. Probes having a higher affinity for GLP-1R have been desired, and a large number of radioactive probes utilizing an Exendin skeleton are being studied. Therefore, an object of the present disclosure is to provide a peptide that can be used as an imaging probe for GLP-1R and that has a high affinity for GLP-1R.

Means for Solving the Problem

The present disclosure, in one aspect, the present disclosure relates to a polypeptide represented by the following formula (1);

(Sequence ID No. 1)
Xaa$_1$-Leu-Ser-Lys-Gln-Met-Glu-Glu-Glu-Ala-Val-Arg-
Leu-Phe-Ile-Glu-Trp-Leu-Lys-Asn-Gly-Gly-Pro-Ser-
Ser-Gly-Ala-Pro-Pro-Pro-Ser  (1)

where Xaa$_1$ represents an aspartic acid in which a —Y—X group binds to an α-amino group, X represents diethylenetriaminepentaacetic dianhydride (DTPA) or 1,4,7-triazacyclononnane-N,N',N"-triacetic acid (NOTA), and Y represents a linker including a group selected from the group consisting of —CH$_2$—(C$_6$H$_4$)—, —NH—C(=S)—, —NH—(CH$_2$)$_5$—C(=O)—, and a combination thereof.

The present disclosure, in one aspect, relates to a polypeptide represented by the following formula (2).

(Sequence ID No. 2)

(2)

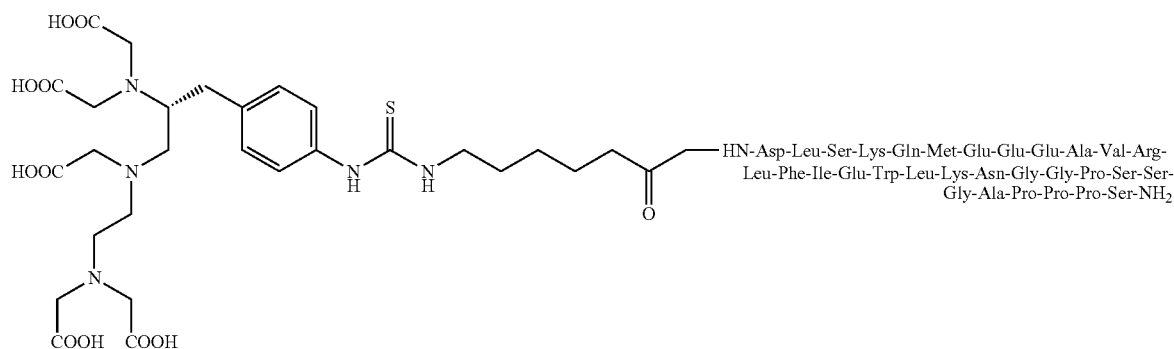

The present disclosure, in one aspect, the present disclosure relates to a polypeptide represented by the following formula (3);

(Sequence ID No. 3)
Xaa$_1$-Leu-Ser-Lys-Gln-Met-Glu-Glu-Glu-Ala-Val-Arg-
Leu-Phe-Ile-Glu-Trp-Leu-Lys-Asn-Gly-Gly-Pro-Ser-
Ser-Gly-Ala-Pro-Pro-Pro-Ser  (3)

where Xaa$_1$ represents an aspartic acid in which a —Y—X' group binds to an α-amino group, X' includes a chelating site and a radioactive metal nuclide chelated by the chelating site, the chelating site being diethylenetriaminepentaacetic dianhydride (DTPA) or 1,4,7-triazacyclononnane-N,N',N"-triacetic acid (NOTA), and Y represents a linker including a group selected from the group consisting of —CH$_2$—(C$_6$H$_4$)—, —NH—C(=$_S$)—, —NH—(CH$_2$)$_5$—C(=O)—, and a combination thereof.

The present disclosure, in one aspect, the present disclosure relates to a polypeptide represented by the following formula (4).

(Sequence ID No. 4)

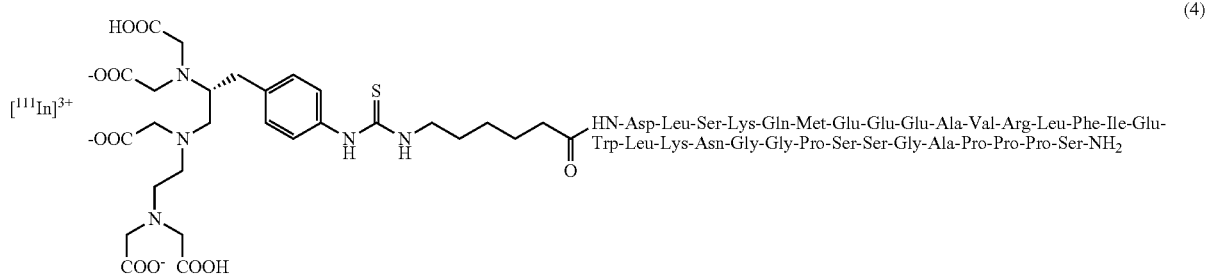

(4)

The present disclosure, in one aspect, the present disclosure relates to a polypeptide represented by the following formula (5);

(Sequence ID No. 5)
Asp-Leu-Ser-Xaa$_4$-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser (5)

where Xaa$_4$ represents a lysine residue in which a —Y—X group binds to an amino group in a side chain, X represents diethylenetriaminepentaacetic dianhydride (DTPA) or 1,4,7-triazacyclononnane-N,N',N"-triacetic acid (NOTA), and Y represents a linker including a group selected from the group consisting of —CH$_2$—(C$_6$H$_4$)—, —NH—C(=S)—, —NH—(CH$_2$)$_5$—C(=O)—, and a combination thereof.

The present disclosure, in one aspect, the present disclosure relates to a polypeptide represented by the following formula (6).

(Sequence ID No. 6)

The present disclosure, in one aspect, the present disclosure relates to a polypeptide represented by the following formula (7);

(Sequence ID No. 7)
Asp-Leu-Ser-Xaa$_4$-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser (7)

where Xaa$_4$ represents a lysine residue in which a —Y—X' group binds to an amino group in a side chain, X' includes a chelating site and a radioactive metal nuclide chelated by the chelating site, the chelating site being diethylenetriaminepentaacetic dianhydride (DTPA) or 1,4,7-triazacyclononnane-N,N',N"-triacetic acid (NOTA), and Y represents a linker including a group selected from the group consisting of —CH$_2$—(C$_6$H$_4$)—, —NH—C(=S)—, —NH—(CH$_2$)$_5$—C(=O)—, and a combination thereof.

The present disclosure, in one aspect, the present disclosure relates to a polypeptide represented by the following formula (8).

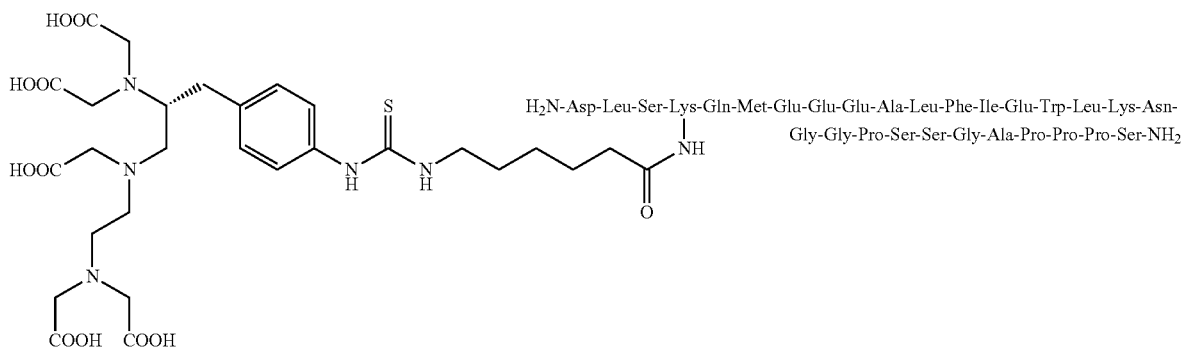

(6)

(Sequence ID No. 8)

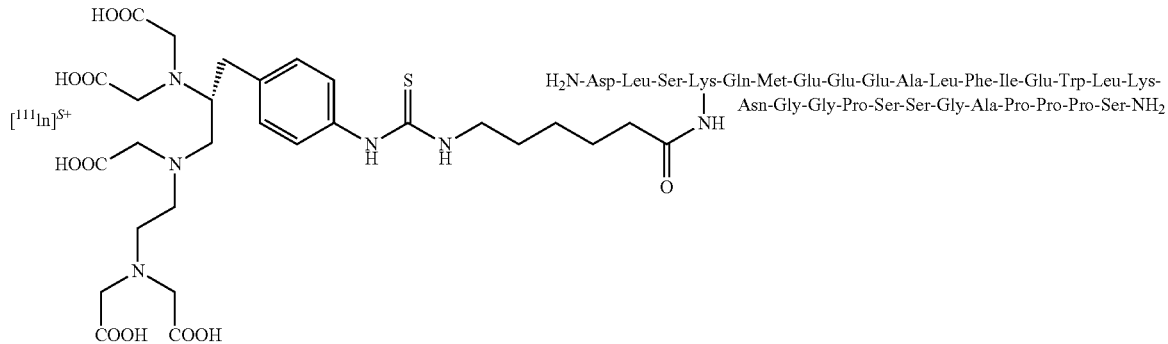

(8)

The present disclosure, in one aspect, the present disclosure relates to a polypeptide represented by the following formula (19);

a polypeptide represented by the formula (19) in which one, two or three amino acids are deleted, added, or substituted, the polypeptide being capable of binding to GLP-1R; or a polypeptide having an amino acid sequence having 85% or more homology to that of the polypeptide represented by the formula (19), the polypeptide being capable of binding to GLP-1R;

The present disclosure, in one aspect, the present disclosure relates to a polypeptide represented by the following formula (20);

a polypeptide represented by the formula (20) in which one, two or three amino acids are deleted, added, or substituted, the polypeptide being capable of binding to GLP-1R; or a polypeptide having an amino acid sequence having 85% or more homology to that of the polypeptide represented by the formula (20), the polypeptide being capable of binding to GLP-1R.

(Sequence ID No. 20)

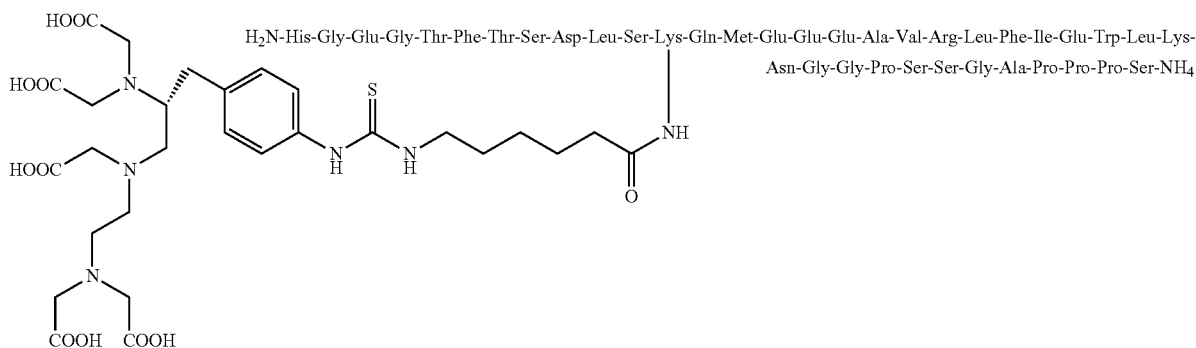

(20)

(Sequence ID No. 19)
His-Gly-Glu-Gly-Thr-Phe-Thr-Ser-Asp-Leu-Ser-Xaa₁₂-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-

Pro-Pro-Pro-Ser (19)

where $Xaa_{12}$ represents a lysine residue in which a —Y—X group binds to an amino group in a side chain, X represents diethylenetriaminepentaacetic dianhydride (DTPA) or 1,4,7-triazacyclononnane-N,N',N"-triacetic acid (NOTA), and Y represents a linker including a group selected from the group consisting of —CH₂—(C₆H₄)—, —NH—C(=S)—, —NH—(CH₂)₅—C(=O)—, and a combination thereof.

The present disclosure, in one aspect, the present disclosure relates to a polypeptide represented by the following formula (21);

a polypeptide represented by the formula (21) in which one, two or three amino acids are deleted, added, or substituted, the polypeptide being capable of binding to GLP-1R; or a polypeptide having an amino acid sequence having 85% or more homology to that of the polypeptide represented by the formula (21), the polypeptide being capable of binding to GLP-1R;

(Sequence ID No. 21)
His-Gly-Glu-Gly-Thr-Phe-Thr-Ser-Asp-Leu-Ser-Xaa₁₂-

Gln-Met-Glu-Glu-Glu-Ala-Val-Arg-Leu-Phe-Ile-Glu-

-continued

```
Trp-Leu-Lys-Asn-Gly-Gly-Pro-Ser-Ser-Gly-Ala-
Pro-Pro-Pro-Ser (21)
``` where $Xaa_{12}$ represents a lysine residue in which a —Y—X' group binds to an amino group in a side chain, X' includes a chelating site and a radioactive metal nuclide chelated by the chelating site, the chelating site being diethylenetriaminepentaacetic dianhydride (DTPA) or 1,4,7-triazacyclononnane-N,N',N"-triacetic acid (NOTA), and Y represents a linker including a group selected from the group consisting of —CH$_2$—(C$_6$H$_4$)—, —NH—C(=S)—, —NH—(CH$_2$)$_5$—C(=O)—, and a combination thereof.

The present disclosure, in one aspect, the present disclosure relates to a polypeptide represented by the following formula (22);

a polypeptide represented by the formula (22) in which one, two or three amino acids are deleted, added, or substituted, the polypeptide being capable of binding to GLP-1R; or a polypeptide having an amino acid sequence having 85% or more homology to that of the polypeptide represented by the formula (22), the polypeptide being capable of binding to GLP-1R.

(Sequence ID No. 22)

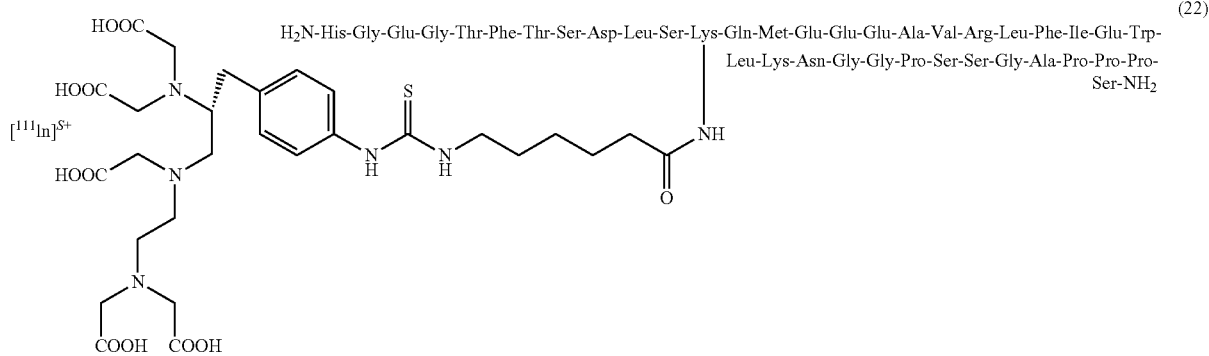

The present disclosure, in another aspect, the present disclosure relates to a composition for imaging including the polypeptide according to the present disclosure. The present disclosure, in another aspect, the present disclosure relates to an imaging method including detecting radioactive signals of the polypeptide according to the present disclosure from a subject to which the polypeptide has been administered. The present disclosure, in another aspect, the present disclosure relates to use of the polypeptide according to the present disclosure.

Effects of the Invention

With the present disclosure, it is possible to provide a peptide that can be used as an imaging probe for GLP-1R and that has a high affinity for GLP-1R.

DESCRIPTION OF THE INVENTION

Figure 1:
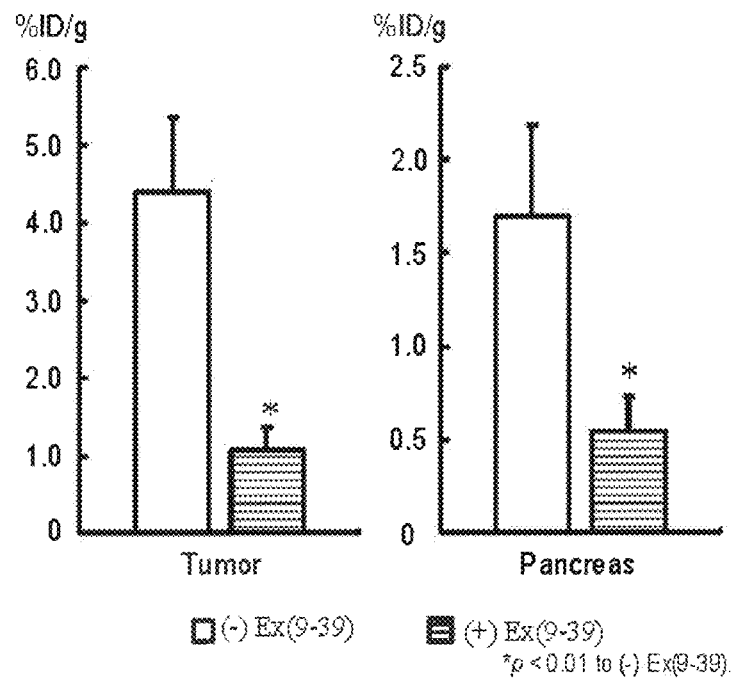
FIG. 1 is a graph showing an example of results of a blocking study using a polypeptide represented by the formula (4).

[Polypeptide to be Used as a Labeling Precursor]

In one or a plurality of embodiments, the present disclosure relates to a polypeptide that can be used as a labeling precursor and that is represented by the following formula (1).

```
                                    (Sequence ID No. 1)
Xaa₁-Leu-Ser-Lys-Gln-Met-Glu-Glu-Glu-Ala-Val-Arg-
Leu-Phe-Ile-Glu-Trp-Leu-Lys-Asn-Gly-Gly-Pro-Ser-
Ser-Gly-Ala-Pro-Pro-Pro-Ser  (1)
```

In the formula (1), $Xaa_1$ represents an aspartic acid in which a —Y—X group binds to the α-amino group. X represents a chelating site constituted by DTPA or NOTA. Y represents a linker that binds to the N-terminal α-amino group of the aspartic acid located at the N terminus of the polypeptide represented by the formula (1) and that includes a group selected from the group consisting of —CH$_2$—(C$_6$H$_4$)—, —NH—C(=S)—, —NH—(CH$_2$)$_5$—C(=O)—, and a combination thereof. In one or a plurality of embodiments, Y preferably includes —CH$_2$—(C$_6$H$_4$)— and —NH—C(=S)—, more preferably includes —CH$_2$—(C$_6$H$_4$)—, —NH—C(=S)— and —NH—(CH$_2$)$_5$—C(=O)—, and even more preferably represents —CH$_2$—(C$_6$H$_4$)—NH—C(=S)—NH—(CH$_2$)$_5$—C(=O)—. That is, in the formula (1), $Xaa_1$ represents an aspartic acid having the above-described linker, and DTPA or NOTA, and one end of the linker binds to the N-terminal α-amino group of the aspartic acid and the other end thereof binds to the DTPA or the NOTA.

In one or a plurality of embodiments, the present disclosure relates to a polypeptide that can be used as a labeling precursor and that is represented by the following formula (5).

(Sequence ID No. 5)
Asp-Leu-Ser-Xaa$_4$-Gln-Met-Glu-Glu-Glu-Ala-Val-Arg-

Leu-Phe-Ile-Glu-Trp-Leu-Lys-Asn-Gly-Gly-Pro-Ser-

Ser-Gly-Ala-Pro-Pro-Pro-Ser (5)

In the formula (5), Xaa$_4$ represents a lysine residue in which a —Y—X group binds to the amino group in the side chain. X represents a chelating site constituted by DTPA or NOTA. Y represents a linker that binds to the amino group in the side chain of the lysine and that includes a group selected from the group consisting of —CH$_2$—(C$_6$H$_4$)—, —NH—C(=S)—, —NH—(CH$_2$)$_5$—C(=O)—, and a combination thereof. That is, in the formula (5), Xaa$_4$ represents a lysine residue having the above-described linker, and DTPA or NOTA, and one end of the linker binds to the amino group in the side chain of the lysine residue and the other end thereof binds to the DTPA or the NOTA. In one or a plurality of embodiments, the present disclosure relates to a polypeptide that can be used as a labeling precursor and that is represented by the following formula (19).

(Sequence ID No. 19)
His-Gly-Glu-Gly-Thr-Phe-Thr-Ser-Asp-Leu-Ser-Xaa$_{12}$-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Ser (19)

In the formula (19), Xaa$_{12}$ represents a lysine residue in which a —Y—X group binds to the amino group in the side chain. X represents a chelating site constituted by DTPA or NOTA. Y represents a linker that binds to the amino group in the side chain of the lysine and that includes a group selected from the group consisting of —CH$_2$—(C$_6$H$_4$)—, —NH—C(=S)—, —NH—(CH$_2$)$_5$—C(=O)—, and a combination thereof. That is, in the formula (19), Xaa$_{12}$ represents a lysine residue having the above-described linker, and DTPA or NOTA, and one end of the linker binds to the amino group in the side chain of the lysine residue and the other end thereof binds to the DTPA or the NOTA.

In one or a plurality of embodiments, the present disclosure relates to a polypeptide that can be used as a labeling precursor and that is a polypeptide represented by the above-described formula (19) in which one, two or three amino acids are deleted, added, or substituted. In one or a plurality of embodiments, the polypeptide, which is a polypeptide represented by the above-described formula (19) in which one, two or three amino acids are deleted, added, or substituted, includes Xaa$_{12}$, can bind to GLP-1R, and preferably has the same effect as that of the polypeptide represented by the above-described formula (19).

In one or a plurality of embodiments, the present disclosure relates to a polypeptide that can be used as a labeling precursor and that has an amino acid sequence having 85% or more homology to that of the polypeptide represented by the above-described formula (19). Here, the above-described homology may be calculated using an algorithm that is generally used by a person skilled in the art, such as BLAST or FASTA, or may be based on a number obtained by dividing the number of the same amino acid residues included in two polypeptides to be compared by the total length of one of the two polypeptides (the same applies hereinafter). In one or a plurality of embodiments, the homology can include 85% or more, 86% or more, 87% or more, 88% or more, 89% or more, 90% or more, 91% or more, 92% or more, 93% or more, 94% or more, or 95% homology. In one or a plurality of embodiments, the polypeptide having 85% or more homology includes Xaa$_{12}$, can bind to GLP-1R, and preferably has the same effect as that of the polypeptide represented by the above-described formula (19).

In one or a plurality of embodiments, the present disclosure relates to a polypeptide represented by the following formula (20), a polypeptide represented by the following formula (20) in which one, two or three amino acids are deleted, added, or substituted, or a polypeptide that has an amino acid sequence having 85% or more homology to that of the polypeptide represented by the following formula (20). The homology is as described above.

(Sequence ID No. 20)

(20)

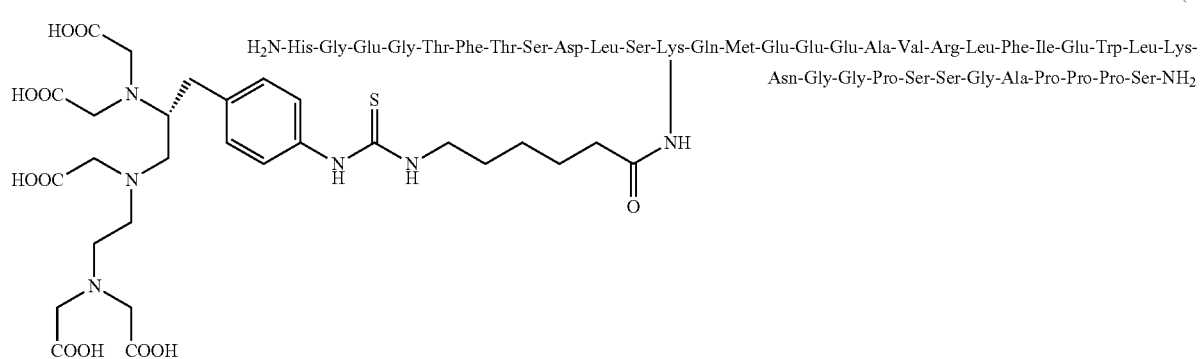

In one or a plurality of embodiments, a polypeptide represented by the formula (20) in which one, two or three amino acids are deleted, added, or substituted, and a polypeptide that has an amino acid sequence having 85% or more homology to that of the polypeptide represented by the formula (20) include $Xaa_{12}$, can bind to GLP-1R, and preferably have the same effect as that of the polypeptide represented by the above-described formula (20).

In one or a plurality of embodiments, a polypeptide to be used as a labeling precursor according to the present disclosure has an amidated C-terminal carboxyl group. The polypeptide of this embodiment can have excellent blood clearance.

A polypeptide to be used as a labeling precursor according to the present disclosure can bind to GLP-1R. In one or a plurality of embodiments, the polypeptide to be used as a labeling precursor according to the present disclosure shows a higher affinity for GLP-1R than non-labeled exendin(9-39) shows. Accordingly, in one or a plurality of embodiments, the polypeptide to be used as a labeling precursor according to the present disclosure can be used as a labeling precursor for a radiolabeling reagent that can be used in imaging or quantification of GLP-1R positive cells, a diagnosis or treatment of diseases related to the expression of GLP-1R, and the like.

There is no particular limitation on a method for manufacturing a polypeptide to be used as a labeling precursor according to the present disclosure. The polypeptide to be used as a labeling precursor according to the present disclosure can be manufactured with reference to a method disclosed in Examples, for example.

[Radiolabeled Polypeptide]

The present disclosure, in another aspect, relates to a polypeptide that is radiolabeled with a radioactive metal nuclide and is represented by the following formula (3).

(Sequence ID No. 3)
$Xaa_1$-Leu-Ser-Lys-Gln-Met-Glu-Glu-Glu-Ala-Val-Arg-

Leu-Phe-Ile-Glu-Trp-Leu-Lys-Asn-Gly-Gly-Pro-Ser-

Ser-Gly-Ala-Pro-Pro-Pro-Ser (3)

In the formula (3), $Xaa_1$ represents an aspartic acid in which a —Y—X' group binds to the α-amino group. X' includes a chelating site and a radioactive metal nuclide chelated by the chelating site. The chelating site is DTPA or NOTA. In one or a plurality of embodiments, examples of the radioactive metal nuclide include $^{62}Cu$, $^{64}Cu$, $^{67}Ga$, $^{68}Ga$, $^{82}Rb$, $^{99m}Tc$, $^{111}In$, and $^{186}Re$. Y represents a linker that binds to the N-terminal α-amino group of the aspartic acid located at the N terminus of the polypeptide represented by the formula (3) and that includes a group selected from the group consisting of —$CH_2$—($C_6H_4$)—, —NH—C(=S)—, —NH—($CH_2$)$_5$—C(=O)—, and a combination thereof. In one or a plurality of embodiments, Y preferably includes —$CH_2$—($C_6H_4$)— and —NH—C(=S)—, more preferably includes —$CH_2$—($C_6H_4$)—, —NH—C(=S)— and —NH—($CH_2$)$_5$—C(=O)—, and even more preferably represents —$CH_2$—($C_6H_4$)—NH—C(=S)—NH—($CH_2$)$_5$-C(=O)—. That is, in the formula (3), $Xaa_1$ represents an aspartic acid having a linker, and DTPA or NOTA that has chelated a radioactive metal nuclide, and one end of the linker binds to the N-terminal α-amino group of the aspartic acid and the other end thereof binds to the DTPA or the NOTA, which has chelated the radioactive nuclide.

The present disclosure, in another aspect, relates to a polypeptide that is radiolabeled with a radioactive metal nuclide and is represented by the following formula (7).

(Sequence ID No. 7)
Asp-Leu-Ser-$Xaa_4$-Gln-Met-Glu-Glu-Glu-Ala-Val-Arg-

Leu-Phe-Ile-Glu-Trp-Leu-Lys-Asn-Gly-Gly-Pro-Ser-

Ser-Gly-Ala-Pro-Pro-Pro-Ser (7)

In the formula (7), $Xaa_4$ represents a lysine residue in which a —Y—X' group binds to the amino group in the side chain. X' includes a chelating site constituted by DTPA or NOTA and a radioactive metal nuclide chelated by the chelating site. Y represents a linker that binds to the amino group in the side chain of the lysine. That is, in the formula (7), $Xaa_4$ represents a lysine residue having a linker, and DTPA or NOTA that has chelated a radioactive metal nuclide, and one end of the linker binds to the amino group in the side chain of the lysine residue and the other end thereof binds to the DTPA or the NOTA, which has chelated the radioactive nuclide. The radioactive metal nuclide and the linker are the same as those in the above-described formula (3).

In one or a plurality of embodiments, the present disclosure relates to a polypeptide that is radiolabeled with a radioactive metal nuclide and is represented by the following formula (21).

(Sequence ID No. 21)
His-Gly-Glu-Gly-Thr-Phe-Thr-Ser-Asp-Leu-Ser-$Xaa_{12}$-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Ser (21)

In the formula (21), $Xaa_{12}$ represents a lysine residue in which a —Y—X' group binds to the amino group in the side chain. X' includes a chelating site and a radioactive metal nuclide chelated by the chelating site. Y represents a linker that binds to the amino group in the side chain of the lysine. That is, in the formula (21), $Xaa_{12}$ represents a lysine residue having a linker, and DTPA or NOTA that has chelated a radioactive metal nuclide, and one end of the linker binds to the amino group in the side chain of the lysine residue and the other end thereof binds to the DTPA or the NOTA, which has chelated the radioactive nuclide. The radioactive metal nuclide and the linker are the same as those in the above-described formula (3).

In one or a plurality of embodiments, the present disclosure relates to a polypeptide that is radiolabeled with a radioactive metal nuclide and is a polypeptide represented by the above-described formula (21) in which one, two or three amino acids are deleted, added, or substituted. In one or a plurality of embodiments, a polypeptide represented by the above-described formula (21) in which one, two or three amino acids are deleted, added, or substituted includes $Xaa_{12}$, can bind to GLP-1R, and preferably has the same effect as that of the polypeptide represented by the above-described formula (21).

In one or a plurality of embodiments, the present disclosure relates to a polypeptide that has an amino acid sequence having 85% or more homology to that of the polypeptide represented by the above-described formula (21). In one or a plurality of embodiments, the homology can include 85% or more, 86% or more, 87% or more, 88% or more, 89% or more, 90% or more, 91% or more, 92% or more, 93% or more, 94% or more, or 95% homology. In one or a plurality of embodiments, the polypeptide having 85% or more homology includes Xaa$_{12}$, can bind to GLP-1R, and preferably has the same effect as that of the polypeptide represented by the above-described formula (21).

In one or a plurality of embodiments, the present disclosure relates to a polypeptide represented by the following formula (22), a polypeptide represented by the following formula (22) in which one, two or three amino acids are deleted, added, or substituted, the polypeptide being capable of binding to GLP-1R, or a polypeptide that has an amino acid sequence having 85% or more homology to that of the polypeptide represented by the following formula (22) and that can bind to GLP-1R. The homology is as described above.

of embodiments, the radiolabeled polypeptide according to the present disclosure can be used in imaging or quantification of insulinoma, a diagnosis or treatment of insulinoma, and the like.

In one or a plurality of embodiments, the radiolabeled polypeptide according to the present disclosure can be used in a composition to be used in the above-described various types of imaging, a reagent for imaging, a contrast agent, a diagnostic imaging agent, and the like that include the radiolabeled polypeptide according to the present disclosure as an active component. The form of the composition, the diagnostic imaging agent, and the like is not particularly limited, but is a solution or powder in one or a plurality of (Sequence ID No. 22)

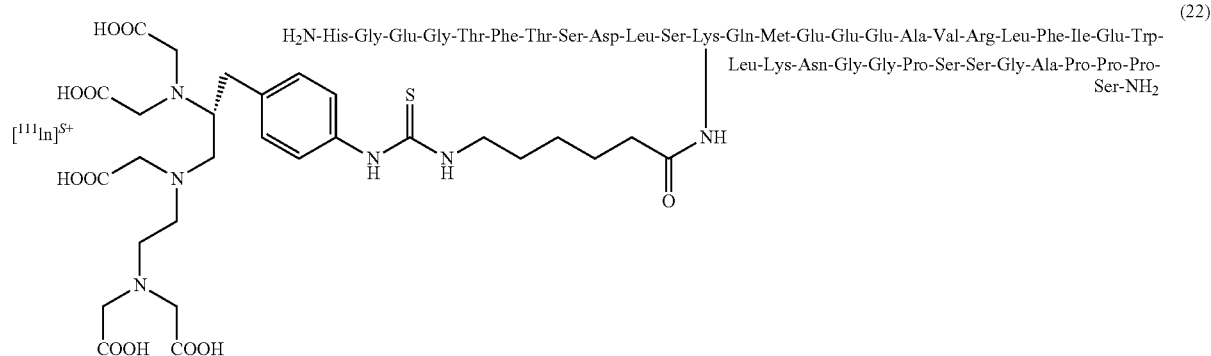

(22)

In one or a plurality of embodiments, a polypeptide represented by the formula (22) in which one, two or three amino acids are deleted, added, or substituted, and a polypeptide that has an amino acid sequence having 85% or more homology to that of the polypeptide represented by the formula (22) include Xaa$_{12}$, can bind to GLP-1R, and preferably have the same effect as that of the polypeptide represented by the above-described formula (22).

In one or a plurality of embodiments, a radiolabeled polypeptide according to the present disclosure has an amidated C-terminal carboxyl group. The polypeptide of this embodiment can have excellent blood clearance.

There is no particular limitation on a method for manufacturing a radiolabeled polypeptide according to the present disclosure. The radiolabeled polypeptide according to the present disclosure can be manufactured with reference to a method disclosed in Examples, for example.

The radiolabeled polypeptide according to the present disclosure can bind to GLP-1R. In one or a plurality of embodiments, the radiolabeled polypeptide according to the present disclosure shows a higher affinity for GLP-1R than non-labeled exendin(9-39) shows. Accordingly, in one or a plurality of embodiments, the radiolabeled polypeptide according to the present disclosure can be used in imaging or quantification of GLP-1R positive cells, a diagnosis or treatment of diseases related to the expression of GLP-1R, and the like. In one or a plurality of embodiments, one example of imaging of GLP-1R positive cells is imaging of pancreatic islet cells. There is no particular limitation on the diseases related to the expression of GLP-1R, and one example thereof is neuroendocrine tumor (NET) in one or a plurality of embodiments. The neuroendocrine tumor is not particularly limited, but is selected from insulinoma, small cell bronchial cancer, and pancreatic cancer in one or a plurality of embodiments. Accordingly, in one or a plurality embodiments. When taking a half-life, radioactivity attenuation, and the like of the radioactive nuclide into consideration, the form thereof is a solution in one or a plurality of embodiments, and the form is an injection in another one or a plurality of embodiments.

[Composition for Imaging]

In yet another aspect, the present disclosure relates to a composition for imaging including the radiolabeled polypeptide according to the present disclosure or the polypeptide to be used as a precursor thereof. The form of the composition for imaging is not particularly limited, but is a solution or powder in one or a plurality of embodiments. In the case where the radiolabeled polypeptide according to the present disclosure is included, when taking a half-life, radioactivity attenuation, and the like of the radioactive nuclide into consideration, the form of the composition for imaging is a solution in one or a plurality of embodiments, and the form is an injection in another one or a plurality of embodiments. In the case where the precursor peptide is included, from the viewpoint of improving the handling, the form of the composition for imaging is powder in one or a plurality of embodiments, and the form is lyophilized powder (lyophilized preparation) in another one or a plurality of embodiments.

The composition for imaging may include a pharmaceutical additive such as a carrier. In the present disclosure, the pharmaceutical additive refers to a compound that is approved and licensed as a pharmaceutical additive by the Japanese Pharmacopoeia, the United States Pharmacopoeia, and/or the European Pharmacopoeia. For example, an aqueous solvent and a non-aqueous solvent can be used as the carrier. Examples of the aqueous solvent include a potassium phosphate buffer, a saline, a Ringer's solution, and distilled water. Examples of the non-aqueous solvent include polyethylene glycol, plant fat and oil, ethanol, glycerin, dimethyl sulfoxide, and propylene glycol.

[Kit]

In yet another aspect, the present disclosure relates to a kit including the polypeptide to be used as a labeling precursor according to the present disclosure and a radioactive metal nuclide, and also to a kit including the radiolabeled polypeptide according to the present disclosure. In one or a plurality of embodiments, the kit of the present disclosure is selected from a kit for manufacture of the radiolabeled polypeptide according to the present disclosure, a kit for imaging of GLP-1R, a kit for imaging of insulinoma, a kit for quantification of GLP-1R positive cells, and a kit for prevention, treatment or diagnosis of insulinoma. In one or a plurality of embodiments, the kit includes an instruction manual corresponding to the form of each embodiment. The instruction manual may be packed with the kit or may be provided on the Web. In one or a plurality of embodiments, the kit further includes a container for storing the radiolabeled polypeptide according to the present disclosure or a precursor thereof. Examples of the container include a syringe and a vial. In one or a plurality of embodiments, the kit according to the present disclosure further includes one or more selected from a component, such as a buffer or an osmotic pressure-adjusting agent, to be used to prepare a molecular probe, and an instrument, such as a syringe, to be used in the administration of the polypeptide.

In yet another aspect, the present disclosure relates to an imaging method that is a method for imaging GLP-1R and that includes detecting radioactive signals of the radiolabeled polypeptide according to the present disclosure from a subject to which the polypeptide has been administered. The subject is not particularly limited, but is selected from a human, a mammal other than a human, a cultured cell, and an object in which GLP-1R can exist.

The imaging method according to the present disclosure includes, as a first embodiment, detecting radioactive signals of the radiolabeled polypeptide according to the present disclosure from a subject to which the polypeptide has been administered in advance. It is preferable to detect the signals after enough time to detect the signals passes from the administration of the polypeptide form, for example.

The imaging method according to the present disclosure includes reconstructing detected signals, converting the signals to images and then displaying the images, and/or presenting an accumulation amount by quantifying the detected signals. In the present disclosure, "displaying" includes displaying the images on a monitor and/or printing the images in one or a plurality of embodiments. In the present disclosure, "presenting" includes storing the calculated accumulation amount and/or outputting the calculated accumulation amount to the outside in one or a plurality of embodiments.

The detection of the signals can be determined as appropriate in accordance with the type of the radioactive nuclide in the polypeptide to be used, and can be performed using PET or SPECT, for example. SPECT includes measuring, with a gamma camera, γ rays emitted from a subject to which the radiolabeled polypeptide according to the present disclosure has been administered. The measurement using a gamma camera includes measuring radiation (γ rays) emitted from a radioactive nuclide in the polypeptide every set period of time, for example, and preferably includes measuring the direction in which radiation is emitted and radiation quantity every set period of time. The imaging method according to the present disclosure may further include displaying the measured distribution of the polypeptides obtained by the measurement of radiation as cross-sectional images and reconstructing the obtained cross-sectional images.

PET includes simultaneously counting, with a PET detector, gamma rays generated due to the pair annihilation of positrons and electrons in a subject to which the polypeptide has been administered, for example, and may further include rendering a three-dimensional distribution of positions of the radioactive nuclides emitting positrons based on the measurement results.

The measurement using X-ray CT and/or MRI may be performed in addition to the measurement using SPECT or PET. This makes it possible to obtain an integrated image in which an image obtained by SPECT or PET (functional image) and an image obtained by CT or MRI (morphological image) are integrated, for example.

The imaging method according to the present disclosure includes, as a second embodiment, administering the radiolabeled polypeptide according to the present disclosure to a subject and detecting the radioactive signals of the polypeptide from the subject to which the polypeptide has been administered. The detection of the signals, the reconstruction of the signals, and the like can be performed in the same manner as in the first embodiment.

The polypeptide may be topically or systemically administered to a subject. The administration route can be determined as appropriate in accordance with a condition of the subject and the like, and examples thereof include an intravenous injection or infusion, an arterial injection or infusion, an intradermal injection or infusion, and an abdominal injection or infusion. The administration amount (dosage) of the polypeptide is not particularly limited. It is sufficient to administer the polypeptide in an amount enough to obtain the desired contrast for imaging. In one or a plurality of embodiments, it is possible to set the administration amount to 1 µg or less. In one or a plurality of embodiments, the radiolabeled polypeptide according to the present disclosure is administered together with a pharmaceutical additive such as a carrier. The pharmaceutical additive is as described above. For example, the time between the administration and the measurement can be determined as appropriate in accordance with the time required for the polypeptide to bind to GLP-1R, the type of the polypeptide, the degradation time of the polypeptide, and the like.

In one or a plurality of embodiments, the imaging method of the second embodiment includes determining an expression state of GLP-1R based on the results of imaging using the radiolabeled polypeptide according to the present disclosure. In one or a plurality of embodiments, the determination of an expression state of GLP-1R includes determining whether or not GLP-1R is expressed and/or determining whether the number of GLP-1R positive cells increases or decreases, by analyzing the images obtained by imaging GLP-1R.

In yet another aspect, the present disclosure relates to a method for measuring the quantity of insulinoma cells that includes detecting the radioactive signals of the radiolabeled polypeptide according to the present disclosure from a subject to which the polypeptide has been administered and calculating the quantity of insulinoma cells from the detected signals of the polypeptide. The quantity of insulinoma cells can be calculated by analyzing the amount of the detected signals or the imaging images obtained by reconstructing the signals, for example. Moreover, a person skilled in the art can easily quantify the imaging object from the imaging results by using a calibration curve or an appropriate program, for example. The method for measuring the quantity of insulinoma cells may further include displaying and/or presenting the calculated quantity of insulinoma cells.

[Method for Preventing, Treating, or Diagnosing Diabetes]

In yet another aspect, the present disclosure relates to a method for preventing, treating, or diagnosing diabetes. During a process of diabetes onset, the quantity of pancreatic islet cells (in particular, the quantity of pancreatic β cells) decreases prior to impaired glucose tolerance, and when diabetes progresses to a stage in which the dysfunction is detected or noticed, it becomes difficult to treat diabetes. However, with the imaging method and/or a method for measuring the quantity of pancreatic islet cells using the radiolabeled polypeptide according to the present disclosure, it is possible to find a decrease in the quantity of pancreatic islet cells and/or pancreatic β cells in an early stage, and in turn, to provide a novel method for preventing, treating, or diagnosing diabetes. Examples of an object of diabetes prevention, treatment, and diagnosis (subject) include a human and/or a mammal other than a human.

The method for diagnosing diabetes according to the present disclosure includes imaging pancreatic β cells using the radiolabeled polypeptide according to the present disclosure and determining a condition of pancreatic islet based on the obtained images of the pancreatic islet and/or the quantity of the islet cells, and may further include diagnosing diabetes based on the determination results. The determination of a condition of pancreatic islet includes determining an increase/decrease or a change in the quantity of the pancreatic islet cells by comparing the obtained images of the pancreatic islet with a reference image of pancreatic islet and by comparing the obtained quantity of the pancreatic islet cells with the reference quantity of pancreatic islet cells, for example. Moreover, the condition of the pancreatic islet may be determined using an information processing device, and it is preferable that when it is determined that the quantity of the pancreatic islet cells decreases, the information is presented, and when it is determined that the quantity of the pancreatic islet cells increases or is maintained, the information is presented. The diagnosis of diabetes based on the determination results includes determining a risk of diabetes onset, determining diabetes, and determining a degree of progress of diabetes, for example.

The method for treating diabetes according to the present disclosure includes imaging pancreatic islet using the radiolabeled polypeptide according to the present disclosure, diagnosing diabetes based on the imaging results, and treating diabetes based on the diagnosis. The imaging of pancreatic islet and the diagnosis of diabetes can be performed in the same manner as in the method for diagnosing diabetes according to the present disclosure. The treatment method can include evaluating an effect of the treatment including administration or diet therapy performed on an object, focusing on a change in the quantity of pancreatic islet cells. Moreover, the method for treating diabetes according to the present disclosure can include imaging pancreatic islet and/or measuring the quantity of pancreatic islet cells by the methods according to the present disclosure and evaluating recovery of functions of the islet cells based on the obtained images of the islet cells and/or the quantity of the islet cells.

The method for preventing diabetes according to the present disclosure includes imaging pancreatic islet using the radiolabeled polypeptide according to the present disclosure, and determining a risk of diabetes onset by determining a condition of the pancreatic islet based on the imaging results. The method for preventing diabetes according to the present disclosure can include checking whether or not the quantity of pancreatic islet cells tends to decrease by measuring the quantity of the pancreatic islet cells periodically, for example.

In another preferable aspect, the present disclosure relates to a method for diagnosing diabetes in a super-early stage. The method for diagnosing diabetes in a super-early stage according to the present disclosure can include imaging pancreatic islet and/or measuring the quantity of pancreatic islet cells by the methods according to the present disclosure in a complete medical checkup or a medical checkup, and determining a condition of the pancreatic islet based on the obtained images of the pancreatic islet and/or the quantity of the pancreatic islet cells, for example.

[Method for Preventing, Treating, or Diagnosing Insulinoma]

In yet another aspect, the present disclosure relates to a method for preventing, treating, or diagnosing insulinoma. With the imaging method and/or a method for measuring the quantity of insulinoma cells using the radiolabeled polypeptide according to the present disclosure, it is possible to find insulinoma in an early stage, and in turn, a method for preventing, treating, or diagnosing insulinoma may be provided. Examples of an object of insulinoma prevention, treatment, and diagnosis (subject) include a human and/or a mammal other than a human.

In one or a plurality of embodiments, the method for diagnosing insulinoma includes imaging GLP-1R using the radiolabeled polypeptide according to the present disclosure, and determining whether or not insulinoma exists based on the obtained images of GLP-1R positive cells and/or the quantity of GLP-1R positive cells. In one or a plurality of embodiments, whether or not insulinoma exists is determined by a step selected from comparing the obtained images of the GLP-1R positive cells with a reference image and comparing the obtained quantity of the GLP-1R positive cells with the reference quantity of GLP-1R positive cells. Moreover, in one or a plurality of embodiments, whether or not insulinoma exists may be determined using an information processing device, and it is preferable that when it is determined that the quantity of the GLP-1R positive cells increases, the information is presented, and when it is determined that the quantity of the GLP-1R positive cells decreases or is maintained, the information is presented. In one or a plurality of embodiments, the diagnosis of insulinoma based on the determination results includes a step selected from determining a risk of insulinoma onset, determining insulinoma, and determining a degree of progress of insulinoma.

The method for treating insulinoma according to the present disclosure includes imaging GLP-1R using the radiolabeled polypeptide according to the present disclosure, diagnosing insulinoma based on the imaging results, and treating insulinoma based on the diagnosis. In one or a plurality of embodiments, the treatment method includes evaluating a treatment effect of administration performed on an object, focusing on a change in the quantity of GLP-1R positive cells.

The method for preventing insulinoma according to the present disclosure includes imaging GLP-1R using the radiolabeled polypeptide according to the present disclosure, and determining a risk of insulinoma onset by determining a condition of the expression of GLP-1R based on the imaging results. The method for preventing insulinoma according to the present disclosure can include checking whether or not the quantity of GLP-1R positive cells tends to decrease by measuring the quantity of the GLP-1R positive cells periodically, for example.

In another preferable aspect, the present disclosure relates to a method for diagnosing insulinoma in a super-early stage. The method for diagnosing insulinoma in a super-early stage according to the present disclosure can include imaging GLP-1R and/or measuring the quantity of GLP-1R positive cells by the methods according to the present disclosure in a complete medical checkup or a medical checkup, and determining a condition of the expression of the GLP-1R based on the obtained images of the GLP-1R positive cells and/or the quantity of the GLP-1R positive cells, for example.

[Labeling Method]

In yet another aspect, the present disclosure relates to a method for labeling a polypeptide to which a chelating site binds. The labeling method according to the present disclosure includes dissolving the polypeptide in a Good's buffer or a buffer containing a nonionic surfactant, and reacting the dissolved polypeptide with an [$^{111}$In] indium salt. With the labeling method according to the present disclosure, even in the case where the concentration of a polypeptide to be labeled is low, it is possible to label the polypeptide at a high radiochemical yield. The concentration of the polypeptide to which a chelating site binds during the reaction with an [$^{111}$In] indium salt is 0.1 to 100 µM in one or a plurality of embodiments, and preferably 0.1 to 50 µM, 0.1 to 10 µM, or 1 to 10 µM.

As the polypeptide to which a chelating site binds, the above-described polypeptide to be used as a labeling precursor can be used in one or a plurality of embodiments, and the polypeptide represented by the formula (1), (2), (5), or (6) can be used in one or a plurality of embodiments that are not particularly limited. In one or a plurality of embodiments, as the polypeptide to which a chelating site binds, the polypeptide represented by the formula (19) or (20) can be used.

droxypropanesulfonic acid (MOPSO), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), N-[tris(hydroxymethyl)methyl]glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO), and N-cyclohexyl-3-aminopropanesulfonic acid (CAPS).

As the nonionic surfactant, polyoxyethylene-p-t-octylphenylether (e.g., Triton based surfactants), polyethylene sorbitan alkyl ester (e.g., Tween based surfactants), and polyoxyethylene alkyl ether (e.g., Brij based surfactants) can be used in one or a plurality of embodiments, and polyoxyethylene sorbitan monolaurate (product name "Tween 80") can be used in one or a plurality of embodiments that are not particularly limited.

The present disclosure can relate to the following one or a plurality of embodiments;

[1] A polypeptide represented by the following formula (1);

(Sequence ID No. 1)
Xaa$_1$-Leu-Ser-Lys-Gln-Met-Glu-Glu-Glu-Ala-Val-Arg-

Leu-Phe-Ile-Glu-Trp-Leu-Lys-Asn-Gly-Gly-Pro-Ser-

Ser-Gly-Ala-Pro-Pro-Pro-Ser (1)

where Xaa$_1$ represents an aspartic acid in which a —Y—X group binds to an α-amino group, X represents diethylenetriaminepentaacetic dianhydride (DTPA) or 1,4,7-triazacyclononnane-N,N',N"-triacetic acid (NOTA), and Y represents a linker including a group selected from the group consisting of —CH$_2$—(C$_6$H$_4$)—, —NH—C(=S)—, —NH—(CH$_2$)$_5$—C(=O)—, and a combination thereof.

[2] A polypeptide represented by the following formula (2);

(Sequence ID No. 2)

(2)

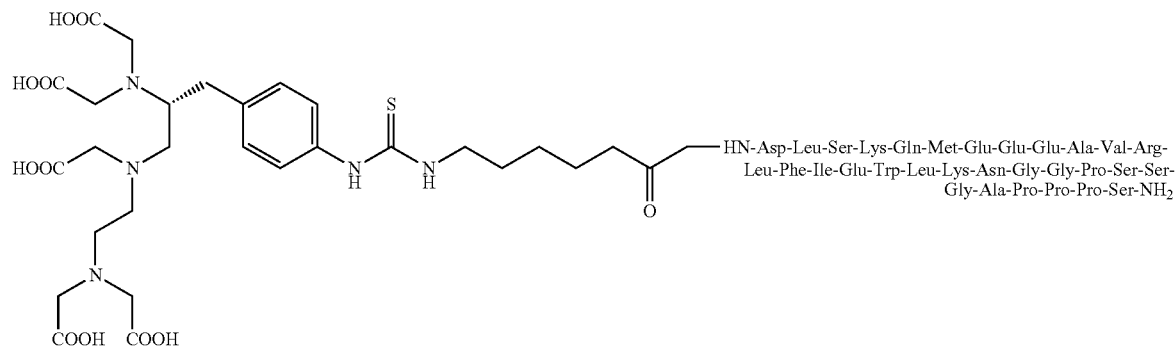

In one or a plurality of embodiments, examples of the buffer include a Good's buffer, acetate buffer, citrate buffer, tartrate buffer, phosphate buffer, and Tris buffer. In one or a plurality of embodiments, examples of the Good's buffer include N,N-bis(2-hydroxyethyl)-2-aminoethanesulfonic acid (BES), 2-morpholinoethanesulfonic acid (MES), bis(2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), 3-morpholino-2-hy-

[3] A polypeptide represented by the following formula (3);

(Sequence ID No. 3)
Xaa$_1$-Leu-Ser-Lys-Gln-Met-Glu-Glu-Glu-Ala-Val-Arg-

Leu-Phe-Ile-Glu-Trp-Leu-Lys-Asn-Gly-Gly-Pro-Ser-

Ser-Gly-Ala-Pro-Pro-Pro-Ser (3)

where $Xaa_1$ represents an aspartic acid in which a —Y—X' group binds to an α-amino group, X' includes a chelating site and a radioactive metal nuclide chelated by the chelating site, the chelating site being diethylenetriamine-pentaacetic dianhydride (DTPA) or 1,4,7-triazacyclonon-nane-N,N',N''-triacetic acid (NOTA), and Y represents a linker including a group selected from the group consisting of —$CH_2$—($C_6H_4$)—, —NH—C(=S)—, —NH—($CH_2$)$_5$—C(=O)—, and a combination thereof.

[4] The polypeptide according to [3], wherein the radioactive metal nuclide is $^{111}$In.

[5] A polypeptide represented by the following formula (4).

(Sequence ID No. 4)

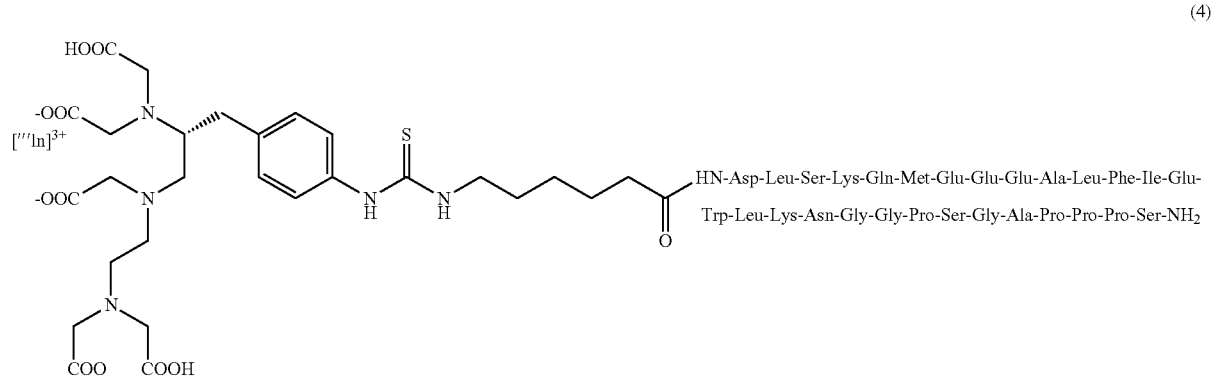

(4)

[6] A polypeptide represented by the following formula (5);

(Sequence ID No. 5)
Asp-Leu-Ser-Xaa$_4$-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser (5)

where $Xaa_4$ represents a lysine residue in which a —Y—X group binds to an amino group in a side chain, X represents diethylenetriaminepentaacetic dianhydride (DTPA) or 1,4,7-triazacyclononnane-N,N',N''-triacetic acid (NOTA), and Y represents a linker including a group selected from the group consisting of —$CH_2$—($C_6H_4$)—, —NH—C(=S)—, —NH—($CH_2$)$_5$—C(=O)—, and a combination thereof.

[7] A polypeptide represented by the following formula (6).

(Sequence ID No. 6)

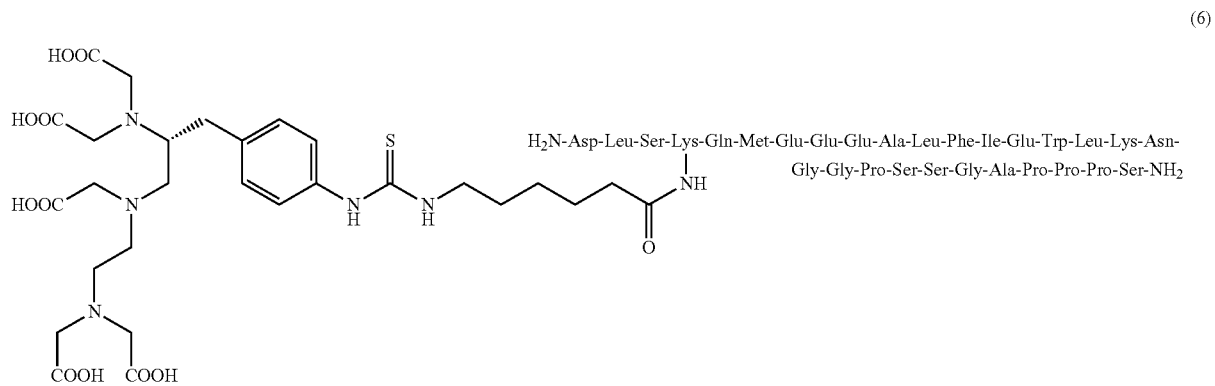

(6)

[8] A polypeptide represented by the following formula (7);

(Sequence ID No. 7)
Asp-Leu-Ser-Xaa₄-Gln-Met-Glu-Glu-Glu-Ala-Val-Arg-
Leu-Phe-Ile-Glu-Trp-Leu-Lys-Asn-Gly-Gly-Pro-Ser-
Ser-Gly-Ala-Pro-Pro-Pro-Ser (7)

where Xaa₄ represents a lysine residue in which a —Y—X' group binds to an amino group in a side chain, X' includes a chelating site and a radioactive metal nuclide chelated by the chelating site, the chelating site being diethylenetriaminepentaacetic dianhydride (DTPA) or 1,4, 7-triazacyclononnane-N,N',N"-triacetic acid (NOTA), and Y represents a linker including a group selected from the group consisting of —CH₂—(C₆H₄)—, —NH—C(=S)—, —NH—(CH₂)₅—C(=O)—, and a combination thereof.

[9] The polypeptide according to [8], wherein the radioactive metal nuclide is ¹¹¹In.

[10] A polypeptide represented by the following formula (8).

(Sequence ID No. 8)

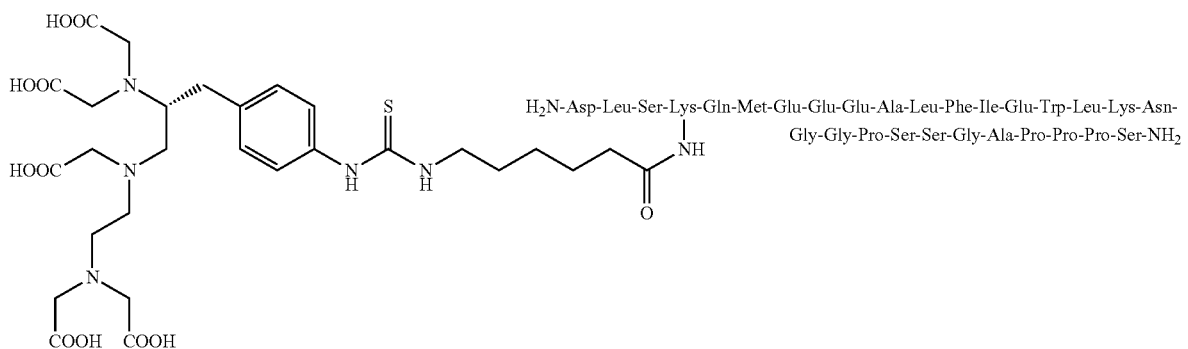

(8)

[11] A composition for imaging containing the polypeptide according to any of [3] to [5] and [8] to [10].

[12] A kit including the polypeptide according to [1], [2], [6], or [7], and a radioactive metal nuclide.

[13] A method for imaging a GLP-1 receptor, including detecting radioactive signals of the polypeptide according to any of [3] to [5] and [8] to [10] from a subject to which the polypeptide has been administered.

[14] The imaging method according to [13], including reconstructing the detected signals, converting the signals to images, and displaying the images.

[15] The polypeptide according to any of [3] to [5] and [8] to [10], which is to be used in the imaging method according to [13] or [14].

[16] Use of the polypeptide according to any of [3] to [5] and [8] to [10] for imaging a GLP-1 receptor.

[17] Use of the polypeptide according to [1], [2], [6], or [7] for manufacturing a composition for imaging to be used in the imaging method according to [13] or [14].

[18] A method for labeling a polypeptide to which a chelating site binds, including dissolving the polypeptide in a Good's buffer or a buffer containing a nonionic surfactant, and reacting the dissolved polypeptide with an [¹¹¹In] indium salt.

[19] A polypeptide represented by the following formula (19);

a polypeptide represented by the formula (19) in which one, two or three amino acids are deleted, added, or substituted, the polypeptide being capable of binding to GLP-1R; or a polypeptide having an amino acid sequence having 85% or more homology to that of the polypeptide represented by the formula (19), the polypeptide being capable of binding to GLP-1R;

(Sequence ID No. 19)
His-Gly-Glu-Gly-Thr-Phe-Thr-Ser-Asp-Leu-Ser-Xaa₁₂-
Gln-Met-Glu-Glu-Glu-Ala-Val-Arg-Leu-Phe-Ile-Glu-
Trp-Leu-Lys-Asn-Gly-Gly-Pro-Ser-Ser-Gly-Ala-Pro-
Pro-Pro-Ser (19)

where Xaa₁₂ represents a lysine residue in which a —Y—X group binds to an amino group in a side chain, X represents diethylenetriaminepentaacetic dianhydride (DTPA) or 1,4,7-triazacyclononnane-N,N',N"-triacetic acid (NOTA), and Y represents a linker including a group selected from the group consisting of —CH₂—(C₆H₄)—, —NH—C(=S)—, —NH—(CH₂)₅—C(=O)—, and a combination thereof.

[20] A polypeptide represented by the following formula (20);

a polypeptide represented by the formula (20) in which one, two or three amino acids are deleted, added, or substituted, the polypeptide being capable of binding to GLP-1R; or a polypeptide having an amino acid sequence having 85% or more homology to that of the polypeptide represented by the formula (20), the polypeptide being capable of binding to GLP-1R.

(Sequence ID No. 20)

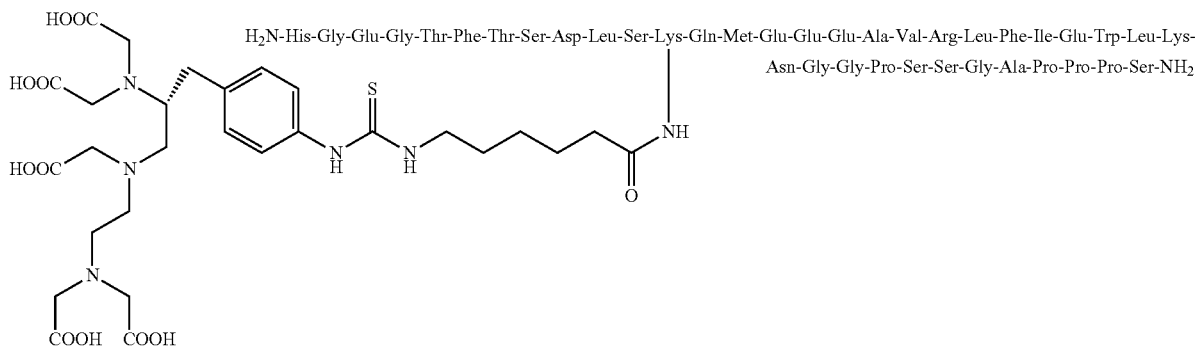

(20)

[21] A polypeptide represented by the following formula (21);
a polypeptide represented by the formula (21) in which one, two or three amino acids are deleted, added, or substituted, the polypeptide being capable of binding to GLP-1R; or
a polypeptide having an amino acid sequence having 85% or more homology to that of the polypeptide represented by the formula (21), the polypeptide being capable of binding to GLP-1R;

[22] A polypeptide represented by the following formula (22);
a polypeptide represented by the formula (22) in which one, two or three amino acids are deleted, added, or substituted, the polypeptide being capable of binding to GLP-1R; or
a polypeptide having an amino acid sequence having 85% or more homology to that of the polypeptide represented by the formula (22), the polypeptide being capable of binding to GLP-1R.

(Sequence ID No. 22)

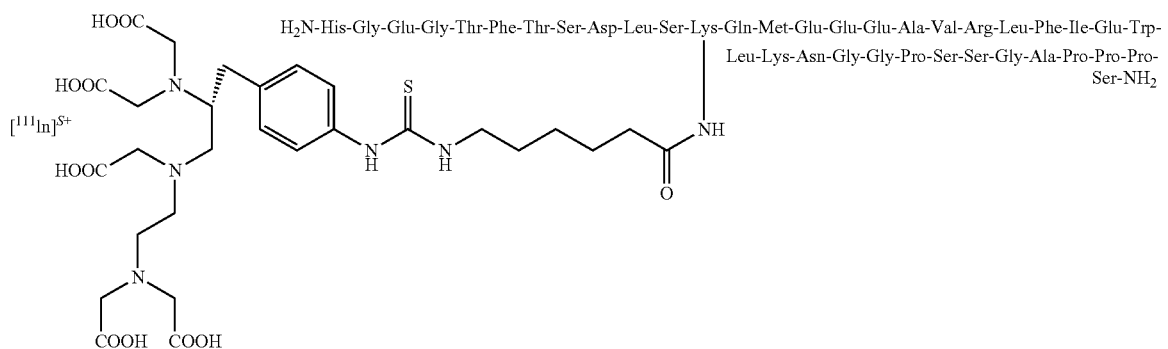

(22)

```
                                    (Sequence ID No. 21)
His-Gly-Glu-Gly-Thr-Phe-Thr-Ser-Asp-Leu-Ser-Xaa12-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Ser  (21)
``` where $Xaa_{12}$ represents a lysine residue in which a —Y—X' group binds to an amino group in a side chain, X' includes a chelating site and a radioactive metal nuclide chelated by the chelating site, the chelating site being diethylenetriaminepentaacetic dianhydride (DTPA) or 1,4,7-triazacyclononnane-N,N',N"-triacetic acid (NOTA), and Y represents a linker including a group selected from the group consisting of —CH$_2$—(C$_6$H$_4$)—, —NH—C(=S)—, —NH—(CH$_2$)$_5$—C(=O)—, and a combination thereof.

[23] A composition for imaging containing the polypeptide according to [21] or [22].
[24] A kit including the polypeptide according to [19] or [20], and a radioactive metal nuclide.
[25] A method for imaging a GLP-1 receptor, including detecting radioactive signals of the polypeptide according to [21] or [22] from a subject to which the polypeptide has been administered.
[26] The imaging method according to [25], including reconstructing the detected signals, converting the signals to images, and displaying the images.
[27] The polypeptide according to [21] or [22], which is to be used in the imaging method according to [25] or [26].
[28] Use of the polypeptide according to [21] or [22] for imaging a GLP-1 receptor.
[29] Use of the polypeptide according to [19] or [20] for manufacturing a composition for imaging to be used in the imaging method according to [25] or [26].

[30] A method for manufacturing a polypeptide according to any of [3] to [5], [8] to [10], [21] and [22], including dissolving the polypeptide according to [1], [2], [6], [7], [19], or [20] in a buffer containing a nonionic surfactant or a Good's buffer, and reacting the dissolved polypeptide with an [$^{111}$In] indium salt.

[31] The manufacturing method according to [30] including dissolving the polypeptide in a Good's buffer containing a nonionic surfactant.

Hereinafter, the present disclosure will be described more specifically by use of examples. It should be noted that the present disclosure should not be construed to be limited to the following examples.

EXAMPLES

It should be noted that the following abbreviations are used in the present disclosure.
Bn: benzyl
Ahx: 6-aminohexanoic acid
OtBu: tert-butyloxy
Fmoc: 9-fluorenylmethyloxycarbonyl group
HBTU: 1-[bisdimethylaminomethylene]-1H-benzotriazolium-3-oxide-hexafluorophosphate
NaOAc: sodium acetate
Trt: trityl
TIS: triisopropyl silane
DT: dodecane thiol It should be noted that L-amino acids were used unless otherwise stated.

Production Example 1

A polypeptide represented by the formula (2) was prepared by the following procedure.

(Sequence ID No. 2)
(Bn DTPA)-

Ahx-DLSKQMEEEAVRLFIEWLKNGGPSSGAPPPS-NH$_2$ (2)

(1) Synthesis of Protected Peptide Resin (Sequence ID No. 9)
(Bn DTPA)-Ahx-DLSKQMEEEAVRLFIEWLKNGGPSSGAPPPS- NH$_2$ Rink Amide MBNA (9)

A protected peptide resin represented by the above-described formula (9) was synthesized by a method for binding amino acids one by one from the carboxyl-terminal side (solid phase synthesis) using an automated peptide synthesizer (431A) manufactured by Applied Biosystems in accordance with a software included therewith.

Rink Amide MBHA Resin (0.25 mmol scale) was used as a starting resin carrier. Fmoc-amino acid derivatives were set in reaction vessels of the peptide synthesizer, and 1-[bisdimethylaminomethylene]-1H-benzotriazolium-3-oxide-hexafluorophosphate (HBTU) and 1-hydroxybenzotriazole (HOBt) serving as activators were dissolved in dimethylformamide (DMF), added to the reaction vessels and reacted, in accordance with the software included with the synthesizer. The resulting resin was moderately stirred in piperidine-containing N-methylpyrrolidone to remove the Fmoc group, and the subsequent condensation of the amino acid derivatives was performed. Among the Fmoc amino acid derivatives used, as the amino acids each having a functional group in the side chain, Asp(OBu), Ser(OBu), Lys(Boc), Gln(Trt), Glu(OBu), Trp(Boc), Arg(Pbf), and Asn(Trt) were used.

Amino acids were successively added according to the sequence to provide a protected peptide resin B represented by the formula (10).

(Sequence ID No. 10)
Fmoc-DLSKQMEEEAVRLFIEWLKNGGPSSGAPPPS-Rink Amide

MBHA (10)

Fmoc-Ahx-OH was introduced to the protected peptide resin B by the HBTU-HOBt method to provide a protected peptide resin C represented by the formula (11).

(Sequence ID No. 11)
Fmoc-Ahx-DLSKQMEEEAVRLFIEWLKNGGPSSGAPPPS-Rink

Amide MBHA (11)

After removing the Fmoc group from the protected peptide resin C, the resulting peptide resin was reacted with p-SCN-Bn-DTPA (manufactured by Macrocyclics) and DIEA to provide the protected peptide resin represented by the formula (9). It should be noted that the notations of the protecting groups in the side chains were omitted in the formulae (9), (10), and (11).

(2) Deprotection and Cutting Out from Resin

The resulting protected peptide resin was treated at room temperature for 2 hours under TFA-TIS-H$_2$O-DT-(95/2.5/2.5/2.5, v/v) deprotection conditions for an ordinary method using trifluoroacetic acid to perform deprotection and cutting out of the peptide from the resin simultaneously. The carrier resin was filtered off from the reaction solution, and then, TFA was distilled off. Ether was added to the residue, and the precipitate of the resulting crude product was collected by filtration.

(3) Isolation and Purification of Peptide of Interest

The resulting crude product peptide was preparatively purified in a water-acetonitrile system containing 0.1% trifluoroacetic acid using an HPLC fractionation device LC-8A manufactured by Shimadzu Corporation (column: ODS 30×250 mm) to provide a fraction of a peptide of interest. After acetonitrile was distilled off, the peptide fraction was made into lyophilized powder to provide the product of interest in the form of its trifluoroacetate salt.

Production Example 2

A polypeptide represented by the formula (12) was prepared by the following procedure.

(Sequence ID No. 12)
(Bn In DTPA)-Ahx-DLSKQMEEEAVRLFIEWLKNGGPSSGAPPPS-

NH$_2$ (12)

The polypeptide represented by the formula (2) (2.7 mg) was dissolved in 100 μL of 0.01 M MES buffer (pH 5.5) containing 0.1% Tween 80, and 20 μL of 1 M InCl$_3$ solution was added thereto. The resulting solution was allowed to stand at room temperature for 5 minutes, and the production of the polypeptide represented by the formula (12) was confirmed by ESI-MASS. The polypeptide was preparatively purified in a water-acetonitrile system containing 0.1% trifluoroacetic acid using an HPLC analysis device LC-20A manufactured by Shimadzu Corporation (column: ODS 10×250 mm) to provide a fraction of a peptide of interest. After acetonitrile was distilled off, the peptide fraction was made into lyophilized powder to provide the polypeptide represented by the formula (12) in the form of its trifluoroacetate salt.

Production Example 3

A polypeptide represented by the formula (6) was prepared by the following procedure.

(Sequence ID No. 6)
DLSK(-Ahx-Bn DTPA)QMEEEAVRLFIEWLKNGGPSSGAPPPS-NH$_2$ (6)

(1) Synthesis of Protected Peptide Resin (Sequence ID No. 13)
Boc-DLSK(-Ahx-Bn DTPA)QMEEEAVRLFIEWLKNGGPSSGAPPPS-Rink Amide MBHA (13)

A protected peptide resin represented by the above-described formula (13) was synthesized by a method for binding amino acids one by one from the carboxyl-terminal side (solid phase synthesis) using an automated peptide synthesizer (431A) manufactured by Applied Biosystems in accordance with a software included therewith.

Rink Amide MBHA Resin (0.25 mmol scale) was used as a starting resin carrier. Fmoc-amino acid derivatives were set in reaction vessels of the peptide synthesizer, and 1-[bisdimethylaminomethylene]-1H-benzotriazolium-3-oxide-hexafluorophosphate (HBTU) and 1-hydroxybenzotriazole (HOBt) serving as activators were dissolved in dimethylformamide (DMF), added to the reaction vessels and reacted, in accordance with the software included with the synthesizer. The resulting resin was moderately stirred in piperidine-containing N-methylpyrrolidone to remove the Fmoc group, and the subsequent condensation of the amino acid derivatives was performed. As the amino acids each having a functional group in the side chain constituting the Fmoc amino acid derivatives used, Asp(OBu), Ser(OBu), Lys(Boc), Lys(Mmt), Gln(Trt), Glu(OBu), Trp(Boc), Arg(Pbf), and Asn(Trt) were used.

Amino acids were successively added according to the sequence to provide a protected peptide resin B represented by the formula (14).

(Sequence ID No. 14)
Boc-DLSK(Mmt)QMEEEAVRLFIEWLKNGGPSSGAPPPS-Rink Amide MBHA (14)

After the protecting group (Mmt group) was removed from the side chain of K12 (the fourth lysine residue) by treatment using 1.5% TFA/5% TIS/93.5% DCM, Fmoc-Ahx-OH was introduced by the HBTU-HOBt method to provide a protected peptide resin C represented by the formula (15).

(Sequence ID No. 15)
Boc-DLSK(-Ahx-Fmoc)QMEEEAVRLFIEWLKNGGPSSGAPPPS-Rink Amide MBHA (15)

Furthermore, after removing the Fmoc group of K(-Ahx-Fmoc)12, the resulting peptide resin was reacted with p-SCN-Bn-DTPA (manufactured by Macrocyclics) and DIEA to provide the protected peptide resin represented by the formula (13). It should be noted that the notations of the protecting groups in the side chains were omitted in the formulae (13), (14), and (15).

(2) Deprotection and Cutting Out from Resin

The resulting protected peptide resin was treated at room temperature for 2 hours under TFA-TIS-H$_2$O-DT-(95/2.5/2.5/2.5, v/v) deprotection conditions for an ordinary method using trifluoroacetic acid to perform deprotection and cutting out of the peptide from the resin simultaneously. The carrier resin was filtered off from the reaction solution, and then, TFA was distilled off. Ether was added to the residue, and the precipitate of the resulting crude product was collected by filtration.

(3) Isolation and Purification of Peptide of Interest

The resulting crude product peptide was preparatively purified in a water-acetonitrile system containing 0.1% trifluoroacetic acid using an HPLC fractionation device LC-8A manufactured by Shimadzu Corporation (column: ODS 30×250 mm) to provide a fraction of a peptide of interest. After acetonitrile was distilled off, the peptide fraction was made into lyophilized powder to provide the product of interest in the form of its trifluoroacetate salt.

Production Example 4

A polypeptide represented by the formula (16) was prepared by the following procedure.

(Sequence ID No. 16)
DLSK(-Ahx-Bn In DTPA)QMEEEAVRLFIEWLKNGGPSSGAPPPS-NH$_2$ (16)

The polypeptide represented by the formula (6) (2.3 mg) was dissolved in 100 µL of 0.01 M MES buffer (pH 5.5) containing 0.1% Tween 80, and 20 µL of 1 M InCl$_3$ solution was added thereto. The resulting solution was allowed to stand at room temperature for 5 minutes, and the production of the polypeptide represented by the formula (16) was confirmed by ESI-MASS. The polypeptide was preparatively purified in a water-acetonitrile system containing 0.1% trifluoroacetic acid using an HPLC analysis device LC-20A manufactured by Shimadzu Corporation (column: ODS 10×250 mm) to provide a fraction of the peptide of interest. After acetonitrile was distilled off, the peptide fraction was made into lyophilized powder to provide the polypeptide represented by the formula (16) in the form of its trifluoroacetate salt.

Conditions for the preparation of a polypeptide represented by the formula (8) were studied by the following procedure.

(Sequence ID No. 8)
DLSK(-Ahx-Bn [$^{111}$In]In DTPA)QMEEEAVRLFIEWLKNGGPSSGAPPPS-NH$_2$ (8)

To each of 20 µL of solutions obtained by dissolving the polypeptide represented by the formula (6) in various solvents (1 to 100 μM), 20 μL of [$^{111}$In]InCl$_3$ (0.02 M HCl) manufactured by Nihon Medi-Physics Co., Ltd. was added. The resulting solution was allowed to stand at room temperature for 30 minutes, and the polypeptide represented by the formula (8) was confirmed in a water-acetonitrile system containing 0.1% trifluoroacetic acid using an HPLC analysis device LC-20A manufactured by Shimadzu Corporation (column: ODS 10×250 mm). Table 1 shows an example of the results.

TABLE 1

| Entry | Precursor Concentration | Solvent | radio-chemical yield(%)[b] |
|---|---|---|---|
| 1 | 100 μM | 0.4M NaOAc (pH 5.0) | >99 |
| 2 | | 0.1M MES (pH 5.5) | >99 |
| 3 | 10 μM | 0.4M NaOAc (pH 5.0) | 13.9 |
| 4 | | 1.0M MES (pH 5.5) | 88.3 |
| 5 | | 0.1M MES (pH 5.5) | 80.3 |
| 6 | | 0.01M MES (pH 5.5) | 24.3 |
| 7 | | H$_2$O | 35.5 |
| 8 | | 0.4M NaOAc (pH 5.0) + 0.1% Tween80 | 70.9 |
| 9 | | 1.0M MES (pH 5.5) + 0.1% Tween80 | 57.5 |
| 10 | | 0.1M MES (pH 5.5) + 0.1% Tween80 | 96.7 |
| 11 | | 0.01M MES (pH 5.5) + 0.1% Tween80 | 97.4 |
| 12 | | 0.1% Tween80aq | 94.5 |
| 13 | 1 μM | 0.4M NaOAc (pH 5.0) | 0 |
| 14 | | 1.0M MES (pH 5.5) | 2.73 |
| 15 | | 0.1M MES (pH 5.5) | 1.2 |
| 16 | | 0.01M MES (pH 5.5) | 2.0 |
| 17 | | H2O | 2.7 |
| 18 | | 0.4M NaOAc (pH 5.0) + 0.1% Tween80 | 20.7 |
| 19 | | 1.0M MES (pH 5.5) + 0.1% Tween80 | 1.5 |
| 20 | | 0.1M MES (pH 5.5) + 0.1% Tween80 | 47.7 |
| 21 | | 0.01M MES (pH 5.5) + 0.1% Tween80 | 86.4 |
| 22 | | 0.1% Tween80aq | 3.2 |

[a] Reaction condition; precursor volume/[$^{111}$In]InCl$_3$ solution volume = 1/1, r.t., 30 min.
[b] Radiochemical yield determined by RP-HPLC analysis.

As shown in Table 1, in the case where the solution of the polypeptide represented by the formula (6) (100 μM) was used, the polypeptide represented by the formula (8) was quantitatively obtained (Entries 1 and 2). In the case where the solution of the polypeptide represented by the formula (6) (10 μM) was used, the radiochemical yield was more favorable when using 0.01 to 1.0 M MES (pH 5.5) as a solvent than when using 0.4 M NaOAc (pH 5.0). In addition, the radiochemical yield was more favorable when adding 0.1% Tween 80 as a solubilizing agent than when not adding 0.1% Tween 80 (Entries 3 to 12). In the case where the solution of the polypeptide represented by the formula (6) (1 μM) was used, no polypeptide represented by the formula (8) was obtained when using 0.4 M NaOAc (pH 5.0) as a solvent (Entry 13), and the radiochemical yield was 1 to 2% even when using 0.01 to 1.0 M MES (pH 5.5) (Entries 14 to 16). In the case where 0.01 M MES (pH 5.5) to which 0.1% Tween 80 was added as a solubilizing agent was used, a favorable radiochemical yield of 86.4% was achieved (Entry 21).

Moreover, when a polypeptide represented by the formula (17) was labeled under the same conditions as shown in Table 1 above, a polypeptide represented by the formula (18) could be prepared similarly.

(Sequence ID No. 17)
HGEGTFTSDLSK(-Ahx-Bn

DTPA)QMEEEAVRLFIEWLKNGGPSSGAPPPS-NH$_2$ (17)

(Sequence ID No. 18)
HGEGTFTSDLSK(-Ahx-Bn [$^{111}$In]In

DTPA)QMEEEAVRLFIEWLKNGGPSSGAPPPS-NH$_2$ (18)

[Procedure of Binding Assay]

Figure 3:
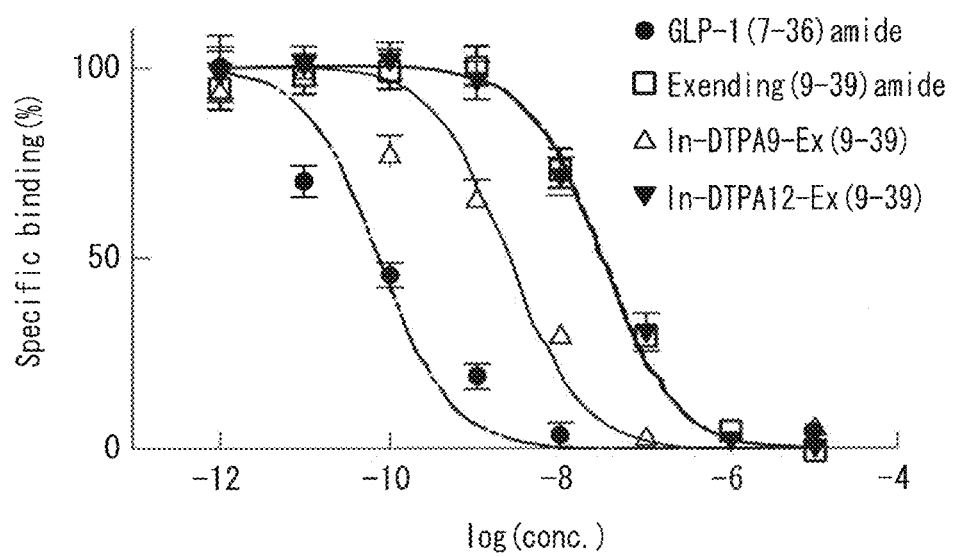
FIG. 3 is a graph showing an example of results of a binding assay.

The mixture of 155 μL of a binding buffer (50 mM HEPES, 5 mM MgCl$_2$, 0.2% BSA, pH 7.4), 20 μL of an aqueous solution of a polypeptide to be evaluated (0, 10$^{-11}$, 10$^{-10}$, 10$^{-9}$, 10$^{-8}$, 10$^{-7}$, 10$^{-6}$, 10$^{-5}$ M), 20 μL of [$^{125}$I]Tyr-GLP-1 (7-36) (5 nM) manufactured by PerkinElmer Co., Ltd., and 5 μL of Membrane Preparation Recombinant Human GLP-1 (200 units/1 mL) manufactured by Millipore was shaken at room temperature for 2 hours. After being shaken, the solution was subjected to B/F separation using a glass fiber filter paper, and the filter paper was washed using a wash buffer (25 mM HEPES, 0.5 M NaCl, 0.1% BSA, pH 7.4). Radioactivity remaining on the filter paper was measured using a γ counter, Wallac 1480 WIZARD® 3, manufactured by PerkinElmer Co., Ltd. The obtained measurement results were analyzed using GraphPad Prism version 5.03 manufactured by GraphPad Software, Inc. A graph in FIG. 3 shows an example of the results.

The IC$_{50}$ of the polypeptide represented by the formula (2) was 6.86 nM, and it was confirmed that the affinity for GLP-1R increased by one digit or more compared with that of non-labeled exendin(9-39) (30.2 nM). Furthermore, the IC$_{50}$ of the polypeptide represented by the formula (12) to which indium had been introduced (In-DTPA9-Ex(9-39)) was 2.5 nM, and the affinity was further increased by introducing indium. The IC$_{50}$ of the polypeptide represented by the formula (6) was 26.25 nM, and it was confirmed that the affinity for GLP-1R was similar to that of non-labeled exendin(9-39) (30.2 nM). Furthermore, the IC$_{50}$ of the polypeptide represented by the formula (16) to which indium had been introduced (In-DTPA12-Ex(9-39)) was 31.27 nM, and it was confirmed that the similar affinity was also obtained by introducing indium.

[In Vitro Evaluation of Stability in Murine Plasma]

Figure 4:
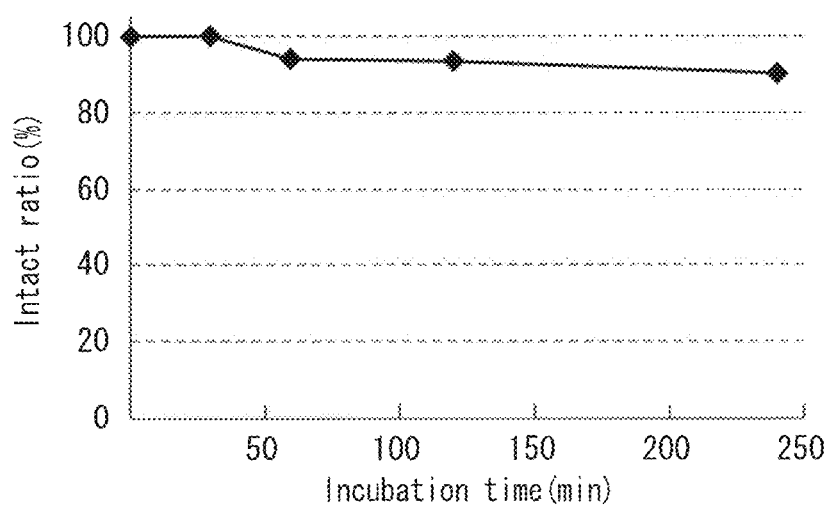
FIG. 4 is a graph showing an example of results of evaluation of the stability of a polypeptide represented by the formula (2) in mouse plasma.

After 200 μL of plasma collected from a ddY mouse (6 weeks old, female) and 20 μL of $^{111}$In-DTPA9-Ex(9-39) (1.85 MBq) were mixed, the resulting mixture was incubated at 37° C. for 30, 60, 120, or 240 minutes. Thereafter, 100 μL of methanol was added to cause aggregation of plasma protein components, and centrifugation was performed for 5 minutes (4° C., 10,000×g) to collect supernatant. The supernatant was filtered using Millex-GV (13 mm), and was analyzed by HPLC. A graph in FIG. 4 shows an example of the results. As shown in FIG. 4, even after the incubation for 240 minutes, 91% of the $^{111}$In-DTPA9-Ex(9-39) existed in the intact form. That is, it could be confirmed that the $^{111}$In-DTPA9-Ex(9-39) was very stable.

Production Example 5

A polypeptide represented by the formula (4) was prepared by the following procedure.

(Sequence ID No. 4)
(Bn [$^{111}$In]In

DTPA)-Ahx-DLSKQMEEEAVRLFIEWLKNGGPSSGAPPPS-NH$_2$ (4)

To 20 µL of a solution (10 µM) obtained by dissolving the polypeptide represented by the formula (2) in 0.01 M MES buffer (pH 5.5) containing 0.1% Tween 80, 20 µL of [$^{111}$In] InCl$_3$ (0.02 M HCl) manufactured by Nihon Medi-Physics Co., Ltd. was added. The resulting solution was allowed to stand at room temperature for 30 minutes. The polypeptide represented by the formula (4) was confirmed in a water-acetonitrile system containing 0.1% trifluoroacetic acid using an HPLC analysis device LC-20A manufactured by Shimadzu Corporation (column: ODS 10×250 mm), and then was used.

Production Example 6

A polypeptide represented by the formula (8) was prepared by the following procedure.

(Sequence ID No. 8)
DLSK(-Ahx-Bn [$^{111}$In]In

DTPA)QMEEEAVRLFIEWLKNGGPSSGAPPPS-NH$_2$ (8)

To 20 µL of a solution (10 µM) obtained by dissolving the polypeptide represented by the formula (6) in 0.01 M MES buffer (pH 5.5) containing 0.1% Tween 80, 20 µL of [$^{111}$In] InCl$_3$ (0.02 M HCl) manufactured by Nihon Medi-Physics Co., Ltd. was added. The resulting solution was allowed to stand at room temperature for 30 minutes. The polypeptide represented by the formula (8) was confirmed in a water-acetonitrile system containing 0.1% trifluoroacetic acid using an HPLC analysis device LC-20A manufactured by Shimadzu Corporation (column: ODS 10×250 mm), and then was used.

[Distribution]

The prepared polypeptide represented by the formula (4) (0.8 to 1.2 µCi) was administered to ddY mice of 6 weeks old (male, 25 g of body weight) by an intravenous injection (caudal vein) without an anesthesia. After 5 minutes, 15 minutes, 30 minutes, 60 minutes, and 120 minutes from the administration, organs were removed (n=5). The weight and radioactivity of each organ were measured, and the accumulation amount (% dose/g) was calculated from the radioactivity per unit weight.

Table 2 below shows an example of the results.

TABLE 2

| | % ID/g ± S.D. | | | | |
|---|---|---|---|---|---|
| | 5 min | 15 min | 30 min | 60 min | 120 min |
| Pancreas | 12.69 ± 3.69 | 9.55 ± 1.80 | 5.74 ± 1.95 | 4.04 ± 0.91 | 2.64 ± 0.77 |
| Blood | 7.92 ± 2.52 | 3.25 ± 0.52 | 1.99 ± 0.31 | 1.19 ± 0.44 | 0.54 ± 0.10 |
| Heart | 3.93 ± 0.85 | 1.86 ± 0.08 | 1.04 ± 0.19 | 1.57 ± 2.38 | 0.26 ± 0.09 |
| Lung | 19.50 ± 3.69 | 13.61 ± 2.60 | 7.75 ± 2.42 | 5.49 ± 1.64 | 4.69 ± 2.20 |
| Stomach | 2.22 ± 1.43 | 1.65 ± 1.03 | 3.01 ± 3.55 | 0.78 ± 0.54 | 9.89 ± 5.62 |
| Small Intestine | 1.91 ± 0.42 | 1.24 ± 0.18 | 1.00 ± 0.26 | 0.75 ± 0.26 | 7.40 ± 5.18 |
| Large Intestine | 1.07 ± 0.28 | 0.80 ± 0.19 | 0.46 ± 0.11 | 0.49 ± 0.17 | 4.14 ± 4.62 |
| Liver | 3.43 ± 0.54 | 2.88 ± 0.24 | 1.60 ± 0.31 | 1.35 ± 0.32 | 1.20 ± 0.28 |
| Spleen | 3.68 ± 0.54 | 2.21 ± 0.45 | 1.11 ± 0.43 | 0.68 ± 0.30 | 0.58 ± 0.20 |
| Kidney | 66.52 ± 8.53 | 69.97 ± 8.19 | 83.71 ± 8.89 | 84.34 ± 8.25 | 83.73 ± 13.86 |

Values are averaged (n = 5) and decay corrected.

As shown in Table 2, the polypeptide represented by the formula (4) accumulated in the pancreas at a level of 12.69% dose/g after 5 minutes from the administration, 9.55% dose/g after 15 minutes from the administration, 5.74% dose/g after 30 minutes from the administration, 4.04% dose/g after 60 minutes from the administration, and 2.64% dose/g after 120 minutes from the administration. Moreover, the polypeptide represented by the formula (4) accumulated in the pancreas at a higher level than in the liver, stomach, spleen, and small intestine, which are adjacent to the pancreas, after 5 to 120 minutes from the administration, thus suggesting that SPECT images having a sufficient contrast for observation could be obtained.

[Distribution]

The prepared polypeptide represented by the formula (6) (0.8 to 1.2 µCi) was administered to ddY mice of 6 weeks old (male, 25 g of body weight) by an intravenous injection (caudal vein) without an anesthesia. After 5 minutes, 15 minutes, 30 minutes, 60 minutes, and 120 minutes from the administration, organs were removed (n=5). The weight and radioactivity of each organ were measured, and the accumulation amount (% dose/g) was calculated from the radioactivity per unit weight. Table 3 below shows an example of the results.

TABLE 3

| | % ID/g ± S.D. | | | | |
| --- | --- | --- | --- | --- | --- |
| | 5 min | 15 min | 30 min | 60 min | 120 min |
| Pancreas | 8.78 ± 2.22 | 4.47 ± 1.08 | 3.27 ± 0.61 | 1.41 ± 0.73 | 0.70 ± 0.16 |
| Blood | 6.24 ± 0.89 | 2.54 ± 0.46 | 1.45 ± 0.32 | 0.52 ± 0.04 | 0.21 ± 0.05 |
| Heart | 3.56 ± 0.47 | 1.41 ± 0.41 | 0.83 ± 0.18 | 0.29 ± 0.07 | 0.15 ± 0.03 |
| Lung | 10.65 ± 1.68 | 7.21 ± 1.47 | 4.93 ± 0.79 | 2.02 ± 0.64 | 1.33 ± 0.57 |
| Stomach | 1.34 ± 0.31 | 0.95 ± 0.69 | 0.95 ± 0.33 | 3.94 ± 2.91 | 7.60 ± 5.55 |
| Small Intestine | 1.83 ± 0.16 | 1.23 ± 0.35 | 2.82 ± 2.79 | 4.98 ± 4.73 | 6.16 ± 3.36 |
| Large Intenstine | 1.43 ± 0.16 | 0.82 ± 0.18 | 0.57 ± 0.27 | 0.27 ± 0.08 | 3.22 ± 2.62 |
| Liver | 2.07 ± 0.12 | 1.34 ± 0.20 | 1.11 ± 0.20 | 0.93 ± 0.24 | 0.80 ± 0.11 |
| Spleen | 2.65 ± 0.30 | 1.29 ± 0.29 | 0.90 ± 0.25 | 0.61 ± 0.15 | 0.49 ± 0.16 |
| Kidney | 53.72 ± 12.28 | 63.18 ± 7.14 | 53.58 ± 4.74 | 67.43 ± 12.12 | 90.75 ± 29.08 |

Values are averaged (n = 5) and decay corrected.

As shown in Table 3, the polypeptide represented by the formula (6) accumulated in the pancreas at a level of 8.78% dose/g after 5 minutes from the administration, 4.47% dose/g after 15 minutes from the administration, 3.27% dose/g after 30 minutes from the administration, 1.41% dose/g after 60 minutes from the administration, and 0.70% dose/g after 120 minutes from the administration. The accumulation amount decreased compared with that of the polypeptide represented by the formula (4), and it was suggested that this was affected by the difference in affinity for GLP-1R. Moreover, the polypeptide represented by the formula (6) accumulated in the pancreas at a higher level than in the liver, stomach, spleen, and small intestine, which are adjacent to the pancreas, after 5 to 30 minutes from the administration, thus suggesting that SPECT images having a sufficient contrast for observation could be obtained.

[Distribution]

The prepared polypeptide represented by the formula (4) (0.8 to 1.2 µCi) was administered to a rat insulinoma cell line INS-1 transplanted BALB/c nu/nu mice (female, 20 g of body weight) by an intravenous injection (caudal vein) without an anesthesia. After 15 minutes, 30 minutes, 60 minutes, 120 minutes, 240 minutes, and 360 minutes from the administration, organs were removed (n=5). The weight and radioactivity of each organ were measured, and the accumulation amount (% dose/g) was calculated from the radioactivity per unit weight. Table 4 below shows an example of the results.

4.40% dose/g after 60 minutes from the administration, 2.32% dose/g after 120 minutes from the administration, 1.87% dose/g after 240 minutes from the administration, and 1.94% dose/g after 360 minutes from the administration. Moreover, the polypeptide represented by the formula (4) accumulated in the pancreas at a higher level than in the liver, stomach, spleen, and small intestine, which are adjacent to the pancreas, after 15 to 360 minutes from the administration, and a ratio INS-1 tumor/pancreas was 2.06 after 15 minutes from the administration, 2.52 after 30 minutes from the administration, 2.70 after 60 minutes from the administration, 2.46 after 120 minutes from the administration, 2.86 after 240 minutes from the administration, and 2.25 after 360 minutes from the administration. These results suggested that SPECT images having a sufficient contrast for observation of the INS-1 tumor could be obtained.

[Blocking Study]

Ex(9-39) amide (20 µg) was administered to a rat insulinoma cell line INS-1 transplanted BALB/c nu/nu mice (female, 20 g of body weight) by an intravenous injection (caudal vein) without an anesthesia. After 30 minutes, the prepared polypeptide represented by the formula (4) (0.8 to 1.2 µCi) was administered. After 60 minutes, organs were removed (n=5). The weight and radioactivity of each organ were measured, and the accumulation amount (% dose/g) was calculated from the radioactivity per unit weight. FIG. 1 shows an example of the results.

TABLE 4

| | % ID/g ± S.D. | | | | | |
| --- | --- | --- | --- | --- | --- | --- |
| | 15 min | 30 min | 60 min | 120 min | 240 min | 360 min |
| INS-1 Tumor | 14.60 ± 1.26 | 7.83 ± 1.86 | 4.40 ± 0.96 | 2.32 ± 0.27 | 1.87 ± 0.52 | 1.94 ± 0.17 |
| Muscle | 1.04 ± 0.22 | 0.51 ± 0.10 | 0.19 ± 0.03 | 0.13 ± 0.02 | 0.09 ± 0.02 | 0.14 ± 0.04 |
| Pancreas | 7.33 ± 1.62 | 3.12 ± 0.56 | 1.70 ± 0.49 | 0.96 ± 0.14 | 0.66 ± 0.20 | 0.88 ± 0.17 |
| Blood | 6.91 ± 1.40 | 3.72 ± 0.43 | 1.75 ± 0.45 | 1.20 ± 0.16 | 0.80 ± 0.11 | 0.55 ± 0.11 |
| Heart | 2.77 ± 0.33 | 1.24 ± 0.28 | 0.55 ± 0.28 | 0.40 ± 0.07 | 0.26 ± 0.05 | 0.24 ± 0.07 |
| Lung | 8.36 ± 1.15 | 3.94 ± 0.64 | 2.79 ± 0.87 | 1.14 ± 0.11 | 0.63 ± 0.09 | 0.48 ± 0.09 |
| Stomach | 2.77 ± 0.96 | 1.93 ± 0.61 | 1.17 ± 0.55 | 0.90 ± 0.59 | 0.50 ± 0.15 | 0.52 ± 0.21 |
| Small Intestine | 2.00 ± 0.26 | 1.58 ± 0.40 | 1.29 ± 0.54 | 1.06 ± 0.65 | 0.58 ± 0.17 | 0.87 ± 0.20 |
| Large Intenstine | 1.18 ± 0.13 | 1.37 ± 1.02 | 2.32 ± 1.13 | 2.59 ± 0.96 | 3.21 ± 0.59 | 2.63 ± 1.04 |
| Liver | 2.52 ± 0.60 | 1.70 ± 0.65 | 1.12 ± 0.17 | 0.97 ± 0.15 | 1.28 ± 0.55 | 1.27 ± 0.36 |
| Spleen | 1.74 ± 0.38 | 1.01 ± 0.24 | 0.72 ± 0.18 | 0.48 ± 0.21 | 0.52 ± 0.15 | 0.69 ± 0.19 |
| Kidney | 180.76 ± 19.82 | 193.57 ± 15.08 | 244.50 ± 22.59 | 229.91 ± 20.03 | 180.88 ± 52.65 | 190.65 ± 19.79 |

Values are averaged (n = 5) and decay corrected.

As shown in Table 4, the polypeptide represented by the formula (4) accumulated in the INS-1 tumor at a level of 14.60% dose/g after 15 minutes from the administration, 7.83% dose/g after 30 minutes from the administration, As shown in FIG. 1, when the accumulation amount (% dose/g) of the polypeptide represented by the formula (4) in the rat insulinoma cell line INS-1 transplanted BALB/c nu/nu mouse to which the Ex(9-39) amide (20 µg) had been administered was compared with the accumulation amount (% dose/g) of the polypeptide represented by the formula (4) in the rat insulinoma cell line INS-1 transplanted BALB/c nu/nu mouse to which no Ex(9-39) amide (20 μg) had been administered, the accumulation amount in the INS-1 tumor decreased by 75.7% and the accumulation amount in the pancreas decreased by 67.7%. Thus, it was confirmed that the polypeptide represented by the formula (4) accumulated specifically to GLP-1R.

[SPECT Study]

Figure 2:
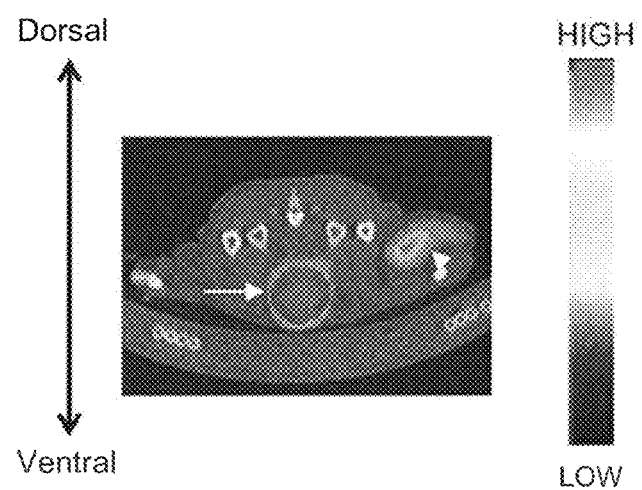
FIG. 2 shows SPECT images obtained by using the polypeptide represented by the formula (4).

The prepared polypeptide represented by the formula (4) (538 μCi) was administered to a rat insulinoma cell line INS-1 transplanted BALB/c nu/nu mouse (female, 20 g of body weight) by an intravenous injection (caudal vein) without an anesthesia. Imaging was performed using a small-animal SPECT/CT (FX-3300) after 30 minutes to 1 hour and 30 minutes from the administration. FIG. 2 shows an example of the results.

FIG. 2 is a caudal transverse view. In FIG. 2, the urinary bladder is indicated by an arrow and the tumor portion is indicated by a triangle. As shown in FIG. 2, the INS-1 tumor could be clearly rendered using the polypeptide represented by the formula (4), and thus three-dimensional imaging became possible. Accordingly, it was suggested that a molecular probe for imaging according to the present invention could be used as a noninvasive imaging probe targeting GLP-1R.

Production Example 7

A polypeptide represented by the formula (20) was prepared by the same procedure as that in Production Example 3. It should be noted that among the Fmoc amino acid derivatives used, as the amino acids each having a functional group in the side chain, His(Trt), Asp(OBu), Ser(OBu), Lys(Boc), Lys(Mmt), Gln(Trt), Glu(OBu), Trp(Boc), Arg(Pbf), and Asn(Trt) were used.

Production Example 8

A polypeptide represented by the formula (23) (also referred to as "In-DTPA12-Ex4" hereinafter) was prepared by the same procedure as that in Production Example 4, except that the polypeptide represented by the formula (20) was used instead of the polypeptide represented by the formula (6).

```
                                           (Sequence ID No. 23)
HGEGTFTSDLSK DLSK(-Ahx-Bn In

DTPA)QMEEEAVRLFIEWLKNGGPSSGAPPPS-NH₂ (23)
```

Production Example 9

A polypeptide represented by the formula (22) (also referred to as "$^{111}$In-DTPA12-Ex4" hereinafter) was prepared by the same procedure as that in Production Example 5, except that the polypeptide represented by the formula (20) was used instead of the polypeptide represented by the formula (2) (radiochemical yield: 64.3%, radiochemical purity: >99%).

```
                                           (Sequence ID No. 22)
HGEGTFTSDLSK(-Ahx-Bn [¹¹¹In]In

DTPA)QMEEEAVRLFIEWLKNGGPSSGAPPPS-NH₂ (22)
```

[Inhibition Assay Using GLP-1 Membrane Preparation]

Figure 5:
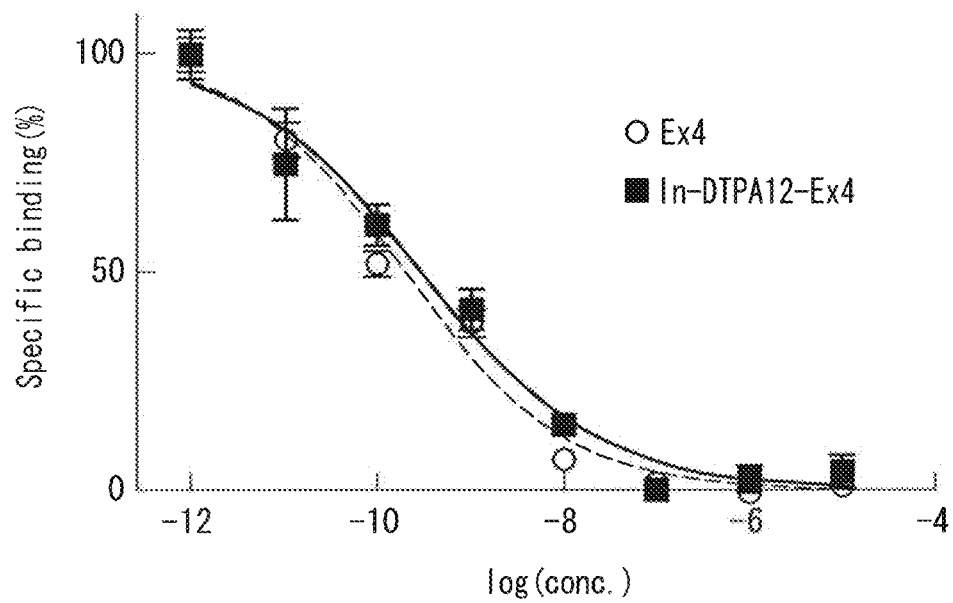
FIG. 5 is a graph showing an example of results of a blocking study using a polypeptide represented by the formula (22).

The mixture of 155 μL of a binding buffer (50 mM HEPES, 5 mM MgCl₂, 0.2% BSA, pH 7.4), 20 μL of an aqueous solution of the In-DTPA12-Ex4 (0, $10^{-11}$, $10^{-19}$, $10^{-9}$, $10^{-8}$, $10^{-7}$, $10^{-6}$, $10^{-5}$M), 20 μL of [$^{125}$I]Tyr-GLP-1 (7-36) (5 nM) manufactured by PerkinElmer Co., Ltd., and 5 μL of Membrane Preparation Recombinant Human GLP-1 (200 units/1 mL) manufactured by Millipore was shaken at 25° C. for 2 hours. After being shaken, the solution was subjected to B/F separation using a glass fiber filter paper, and the filter paper was washed using a wash buffer (25 mM HEPES, 0.5 M NaCl, 0.1% BSA, pH 7.4). Radioactivity remaining on the filter paper was measured using a γ counter, Wallac 1480 WIZARD® 3, manufactured by PerkinElmer Co., Ltd. The obtained measurement results were analyzed using GraphPad Prism version 5.03 manufactured by GraphPad Software, Inc., and the half maximal inhibitory concentration ($IC_{50}$) was determined. A graph in FIG. 5 shows an example of the results. The $IC_{50}$ of the In-DTPA12-Ex4 was 0.43 nM (95% confidence interval: 0.24 to 0.78), and it was confirmed that the binding affinity for GLP-1R was similar to that of non-labeled exendin4 ($IC_{50}$: 0.19 nM (95% confidence interval: 0.11 to 0.32)).

[In Vitro Evaluation of Stability in Murine Plasma]

Figure 6:
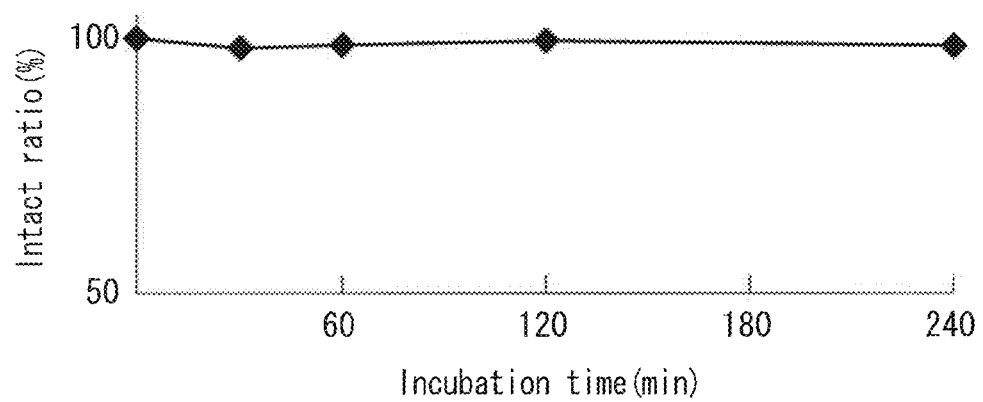
FIG. 6 is a graph showing an example of results of evaluation of the stability of a polypeptide represented by the formula (23) in mouse plasma.

After 200 μL of plasma collected from ddY mice (6 weeks old, female) and 20 μL of $^{111}$In-DTPA12-Ex4 (1.85 MBq) were mixed, the resulting mixtures were incubated at 37° C. for 30, 60, 120, or 240 minutes. Thereafter, 100 μL of methanol was added to cause aggregation of plasma protein components, and centrifugation was performed for 5 minutes (4° C., 10,000×g) to collect supernatant. The supernatant was filtered using Millex-GV (13 mm), and was analyzed by HPLC. A graph in FIG. 6 shows an example of the results. As shown in FIG. 6, even after the incubation for 240 minutes, 98.8% of the $^{111}$In-DTPA12-Ex4 existed in the intact form. That is, it could be confirmed that the $^{111}$In-DTPA12-Ex4 was very stable.

[Cellular Uptake Assay Using INS-1 Tumor Cells]

Figure 7:
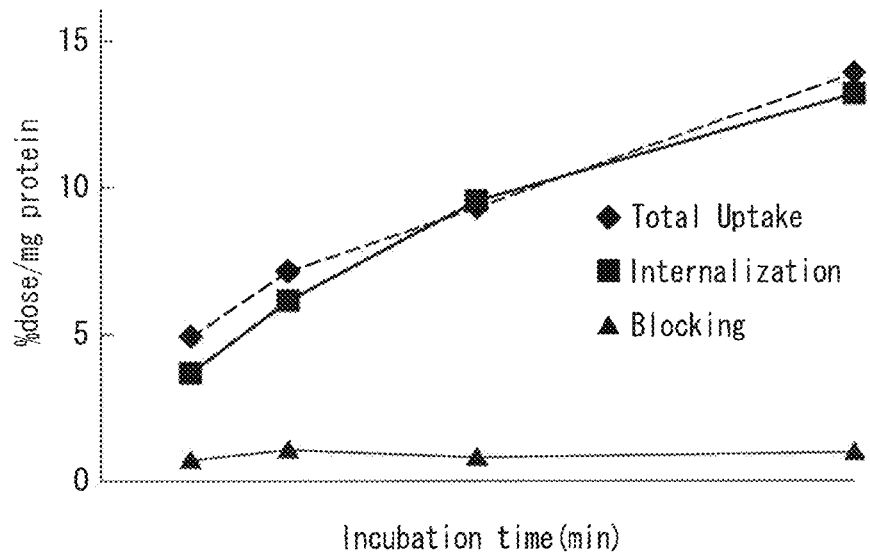
FIG. 7 is a graph showing an example of results of a cell uptake assay using a rat insulinoma cell line INS-1.

After the rat insulinoma cell line INS-1 was seeded in a 24-well plate and was cultured overnight (37° C., 5% CO₂), the $^{111}$In-DTPA12-Ex4 (37 kBq/20 μL) was added, and the mixture was incubated at 37° C. for 30, 60, 120, or 240 minutes. Non-specific binding was evaluated by adding an excessive amount of Exendin-(9-39) together with the polypeptide represented by the formula (23). After the incubation, the cells were washed using a cold PBS(−), and then were lysed using a 0.1 N NaOH aqueous solution. Radioactivity binding to the cell membrane fraction was removed by performing washing and cell lysis after an acid buffer (50 mM glycine, 0.1 M NaCl, pH2.8) was added and the mixture was allowed to stand at 4° C. for 10 minutes. Radioactivity of the cell lysate was corrected by BCA protein assay. FIG. 7 shows an example of the results. In FIG. 7, "Total Uptake" shows an uptake amount (radioactivity) of the polypeptide represented by the formula (23) taken in the cells, "Internalization" shows an uptake amount (radioactivity) after removing radioactivity binding to the cell membrane fraction, and "Blocking" shows the result of evaluation of non-specific binding. As shown in FIG. 7, the amount of the polypeptide represented by the formula (23) taken in the cells increased over time, and the uptake was inhibited by adding excessive amount of exendin-(9-39). Moreover, it was suggested that substantially all the polypeptide represented by the formula (23) binding to GLP-1R existed inside the cells.

[In Vivo Biodistribution]

The $^{111}$In-DTPA12-Ex4 (18.5 kBq/100 μL) was administered to ddY mice (6 weeks old, male) from the caudal vein of the mouse. The mice were killed after 5, 15, 30, 60, or 120 minutes from the administration, and organs (pancreas, blood, heart, lung, stomach, small intestine, large intestine, liver, spleen, and kidney) were removed (n=5). The weight and radioactivity of each organ were measured, and the accumulation amount (% injection dose/g) in each organ was calculated. Table 5 and 6 below show an example of the results.

TABLE 5

| | % ID/g ± S.D. | | | | |
| --- | --- | --- | --- | --- | --- |
| | 5 min | 15 min | 30 min | 60 min | 120 min |
| Pancreas | 16.77 ± 2.58 | 20.45 ± 1.62 | 20.62 ± 3.01 | 20.97 ± 2.14 | 18.28 ± 4.44 |
| Blood | 6.58 ± 0.76 | 2.26 ± 0.31 | 1.22 ± 0.13 | 0.52 ± 0.09 | 0.29 ± 0.03 |
| Heart | 4.54 ± 0.65 | 1.55 ± 0.09 | 1.23 ± 0.15 | 0.73 ± 0.21 | 0.50 ± 0.07 |
| Lung | 36.73 ± 12.57 | 42.98 ± 6.75 | 42.47 ± 10.03 | 36.80 ± 10.04 | 32.07 ± 11.31 |
| Stomach | 2.95 ± 1.50 | 2.33 ± 0.70 | 3.15 ± 3.33 | 3.50 ± 1.31 | 5.06 ± 2.52 |
| Small Intestine | 2.94 ± 0.70 | 1.96 ± 0.33 | 2.12 ± 0.47 | 2.88 ± 0.29 | 4.93 ± 2.48 |
| Large Intestine | 1.46 ± 0.26 | 0.80 ± 0.15 | 0.66 ± 0.06 | 0.56 ± 0.11 | 5.58 ± 6.17 |
| Liver | 3.51 ± 0.42 | 2.33 ± 0.21 | 1.85 ± 0.34 | 1.49 ± 0.10 | 1.58 ± 0.30 |
| Spleen | 3.99 ± 0.63 | 1.74 ± 0.57 | 1.01 ± 0.19 | 0.87 ± 0.14 | 1.03 ± 0.51 |
| Kidoney | 153.22 ± 18.58 | 185.64 ± 14.97 | 213.38 ± 21.90 | 220.45 ± 18.39 | 231.77 ± 21.54 |

Values are averaged (n = 5) and decay correctes.

TABLE 6

| | 5 min | 15 min | 30 min | 60 min | 120 min |
| --- | --- | --- | --- | --- | --- |
| Pancreas/Blood ratio | 2.59 ± 0.56 | 9.16 ± 1.36 | 17.04 ± 3.10 | 41.65 ± 8.43 | 64.01 ± 17.53 |
| Pancreas/Liver ratio | 4.80 ± 0.78 | 8.86 ± 1.19 | 11.27 ± 1.75 | 14.21 ± 2.07 | 12.02 ± 3.80 |

As shown in Table 5, the $^{111}$In-DTPA12-Ex4 accumulated in the pancreas and lung, in which GLP1-R is expressed, at a higher level. As shown in Table 6, the pancreas/blood ratio of the accumulation amount of the $^{111}$In-DTPA12-Ex4 exceeded two in an early stage after the administration, exhibiting favorable blood clearance, and the pancreas/liver ratio of the accumulation amount of the $^{111}$In-DTPA12-Ex4 was very high. It was suggested that with a polypeptide that had a high pancreas/liver ratio of its accumulation amount and excellent blood clearance while accumulating in the pancreas in a high accumulation amount in this manner, clear images could be obtained when imaging pancreatic β cells and preferably imaging GLP-1R in the pancreatic β cells.

[SPECT/CT Study in ddY Mice]

Figure 8:
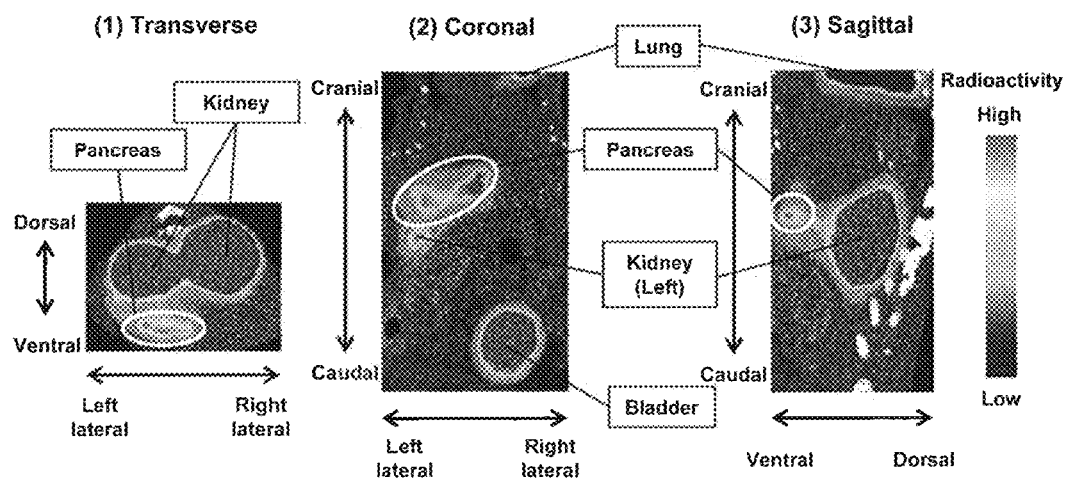
FIG. 8 shows SPECT/CT images obtained by using the polypeptide represented by the formula (22).

The $^{111}$In-DTPA12-Ex4 (9.62 MBq/150 μL) was administered to ddY mice (6 weeks old, male) from the caudal vein of the mouse. After 20 minutes from the administration, the mouse was started to be put under an anesthesia by inhaling isoflurane (2.5%). After 38 minutes from the administration, imaging was started and performed for 48 minutes using a SPECT/CT device (GMI, FX-3300). Thereafter, CT imaging (60 kV, 310 pA) was performed. FIG. 8 shows the results.

Conditions of SPECT Imaging
Method: Tomo
Collimators: 4-head N5F75A10 (1.0-mm diameter, 7.5-mm focal length)
Radius of rotation: 35 mm
Reconstruction: 3D-OSEM (Iterations: 5, Subsets: 8)

FIG. 8 shows a transverse view, a coronal view, and a sagittal view in order from the left. In FIG. 8, the pancreas is located in the position surrounded by a white line. As shown in FIG. 8, the pancreas in a normal mouse (ddy mouse) could be rendered by SPECT/CT imaging using the $^{111}$In-DTPA12-Ex4. Since rendering of the pancreas in a mouse whose pancreas is smaller than that of a human and in which organs are closely spaced was successful in this manner, it was suggested that in a human whose pancreas is larger than that of a mouse and in which organs are not closely spaced, a position and a size of the pancreas can be determined more clearly, and furthermore, the amount of the peptide derivative binding to GLP-1R in the pancreatic β cells can be measured, for example.

It was shown from these results that the $^{111}$In-DTPA12-Ex4 was useful as a GLP-1R binding type pancreatic β cell imaging probe.

INDUSTRIAL APPLICABILITY

A polypeptide according to the present disclosure is useful in a medical research field, a medical field, a non-therapeutic and non-diagnostic field, a molecular imaging field, and an insulinoma-related field, for example.

SEQUENCE LISTING FREE TEXT

Sequence ID No. 1: An embodiment of a polypeptide according to the present disclosure
Sequence ID No. 2: An embodiment of a polypeptide according to the present disclosure
Sequence ID No. 3: An embodiment of a polypeptide according to the present disclosure
Sequence ID No. 4: An embodiment of a polypeptide according to the present disclosure
Sequence ID No. 5: An embodiment of a polypeptide according to the present disclosure
Sequence ID No. 6: An embodiment of a polypeptide according to the present disclosure
Sequence ID No. 7: An embodiment of a polypeptide according to the present disclosure
Sequence ID No. 8: An embodiment of a polypeptide according to the present disclosure Sequence ID No. 9: A protected peptide resin used in an embodiment
Sequence ID No. 10: A protected peptide resin used in an embodiment
Sequence ID No. 11: A protected peptide resin used in an embodiment
Sequence ID No. 12: An embodiment of a polypeptide (cold form) used in an example
Sequence ID No. 13: A protected peptide resin used in an embodiment
Sequence ID No. 14: A protected peptide resin used in an embodiment
Sequence ID No. 15: A protected peptide resin used in an embodiment
Sequence ID No. 16: An embodiment of a polypeptide (cold form) used in an example
Sequence ID No. 17: A polypeptide prepared in an example
Sequence ID No. 18: A polypeptide prepared in an example
Sequence ID No. 19: An embodiment of a polypeptide according to the present disclosure
Sequence ID No. 20: An embodiment of a polypeptide according to the present disclosure
Sequence ID No. 21: An embodiment of a polypeptide according to the present disclosure
Sequence ID No. 22: An embodiment of a polypeptide according to the present disclosure
Sequence ID No. 23: An embodiment of a polypeptide (cold form) used in an example

SEQUENCE LISTING

```
<160> NUMBER OF SEQ ID NOS: 23

<210> SEQ ID NO 1
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Xaa is asparagine

<400> SEQUENCE: 1

Xaa Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Ser
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Alfa-amino group of the N-terminus is bonded to
      DTPA via Ahx-Bn
<220> FEATURE:
<221> NAME/KEY: MOD_RES
<222> LOCATION: (31)..(31)
<223> OTHER INFORMATION: AMIDATION

<400> SEQUENCE: 2

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Ser
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Xaa is asparagine
```

<400> SEQUENCE: 3

Xaa Leu Ser Lys Gln Met Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Alfa-amino group of the N-terminus is bonded to
      [111In]-DTPA via Ahx-Bn
<220> FEATURE:
<221> NAME/KEY: MOD_RES
<222> LOCATION: (31)..(31)
<223> OTHER INFORMATION: AMIDATION

<400> SEQUENCE: 4

Asp Leu Ser Lys Gln Met Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (4)..(4)
<223> OTHER INFORMATION: Xaa is lysine

<400> SEQUENCE: 5

Asp Leu Ser Xaa Gln Met Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (4)..(4)
<223> OTHER INFORMATION: Amino group of the side chain is bonded to DTPA
      via Ahx-Bn
<220> FEATURE:
<221> NAME/KEY: MOD_RES
<222> LOCATION: (31)..(31)
<223> OTHER INFORMATION: AMIDATION

<400> SEQUENCE: 6

Asp Leu Ser Lys Gln Met Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

```
<210> SEQ ID NO 7
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (4)..(4)
<223> OTHER INFORMATION: Xaa is lysine

<400> SEQUENCE: 7

Asp Leu Ser Xaa Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (4)..(4)
<223> OTHER INFORMATION: Amino group of the side chain is bonded to
      [111In]-DTPA via Ahx-Bn
<220> FEATURE:
<221> NAME/KEY: MOD_RES
<222> LOCATION: (31)..(31)
<223> OTHER INFORMATION: AMIDATION

<400> SEQUENCE: 8

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Alfa-amino group of the N-terminus is bonded to
      DTPA via Ahx-Bn. The functional group of the side chain is
      protected by a OBu.
<220> FEATURE:
<221> NAME/KEY: MISC_FEATURE
<222> LOCATION: (3)..(3)
<223> OTHER INFORMATION: The functional group of the side chain is
      protected by a OBu
<220> FEATURE:
<221> NAME/KEY: MISC_FEATURE
<222> LOCATION: (4)..(4)
<223> OTHER INFORMATION: The functional group of the side chain is
      protected by a Boc.
<220> FEATURE:
<221> NAME/KEY: MISC_FEATURE
<222> LOCATION: (5)..(5)
<223> OTHER INFORMATION: The functional group of the side chain is
      protected by a Trt.
<220> FEATURE:
<221> NAME/KEY: MISC_FEATURE
<222> LOCATION: (7)..(9)
<223> OTHER INFORMATION: The functional group of the side chain is
      protected by a OBu.
<220> FEATURE:
<221> NAME/KEY: MISC_FEATURE
```

<222> LOCATION: (12)..(12)
<223> OTHER INFORMATION: The functional group of the side chain is
      protected by a Pdf.
<220> FEATURE:
<221> NAME/KEY: MISC_FEATURE
<222> LOCATION: (17)..(17)
<223> OTHER INFORMATION: The functional group of the side chain is
      protected by a Boc.
<220> FEATURE:
<221> NAME/KEY: MISC_FEATURE
<222> LOCATION: (19)..(19)
<223> OTHER INFORMATION: The functional group of the side chain is
      protected by a OBu.
<220> FEATURE:
<221> NAME/KEY: MISC_FEATURE
<222> LOCATION: (20)..(20)
<223> OTHER INFORMATION: The functional group of the side chain is
      protected by a Trt.
<220> FEATURE:
<221> NAME/KEY: MISC_FEATURE
<222> LOCATION: (24)..(25)
<223> OTHER INFORMATION: The functional group of the side chain is
      protected by a OBu.
<220> FEATURE:
<221> NAME/KEY: MISC_FEATURE
<222> LOCATION: (31)..(31)
<223> OTHER INFORMATION: Carboxyl group of the C-terminus is bound to
      Rink Amide MBHA. Functional group of the side chain is protected
      by a OBu.

<400> SEQUENCE: 9

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: The alfa-amino group of the N-terminus is
      protected by a Fmoc. The functional group of the side chain is
      protected by a OBu.
<220> FEATURE:
<221> NAME/KEY: MISC_FEATURE
<222> LOCATION: (3)..(3)
<223> OTHER INFORMATION: The functional group of the side chain is
      protected by a OBu.
<220> FEATURE:
<221> NAME/KEY: MISC_FEATURE
<222> LOCATION: (4)..(4)
<223> OTHER INFORMATION: The functional group of the side chain is
      protected by a Boc.
<220> FEATURE:
<221> NAME/KEY: MISC_FEATURE
<222> LOCATION: (5)..(5)
<223> OTHER INFORMATION: The functional group of the side chain is
      protected by a Trt.
<220> FEATURE:
<221> NAME/KEY: MISC_FEATURE
<222> LOCATION: (7)..(9)
<223> OTHER INFORMATION: The functional group of the side chain is
      protected by a OBu.
<220> FEATURE:
<221> NAME/KEY: MISC_FEATURE
<222> LOCATION: (12)..(12)
<223> OTHER INFORMATION: The functional group of the side chain is
      protected by a Pdf.
<220> FEATURE:
<221> NAME/KEY: MISC_FEATURE
<222> LOCATION: (17)..(17)

<223> OTHER INFORMATION: The functional group of the side chain is
      protected by a Boc.
<220> FEATURE:
<221> NAME/KEY: MISC_FEATURE
<222> LOCATION: (19)..(19)
<223> OTHER INFORMATION: The functional group of the side chain is
      protected by a OBu.
<220> FEATURE:
<221> NAME/KEY: MISC_FEATURE
<222> LOCATION: (20)..(20)
<223> OTHER INFORMATION: The functional group of the side chain is
      protected by a Trt.
<220> FEATURE:
<221> NAME/KEY: MISC_FEATURE
<222> LOCATION: (24)..(25)
<223> OTHER INFORMATION: The functional group of the side chain is
      protected by a OBu.
<220> FEATURE:
<221> NAME/KEY: MISC_FEATURE
<222> LOCATION: (31)..(31)
<223> OTHER INFORMATION: Carboxyl group of the C-terminus is bound to
      Rink Amide MBHA. The functional group of the side chain is
      protected by a OBu.

<400> SEQUENCE: 10

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: The alfa-amino group of the N-terminus is
      bonded to -Ahx-Fmoc. The functional group of the side chain is
      protected by a OBu.
<220> FEATURE:
<221> NAME/KEY: MISC_FEATURE
<222> LOCATION: (3)..(3)
<223> OTHER INFORMATION: The functional group of the side chain is
      protected by a OBu.
<220> FEATURE:
<221> NAME/KEY: MISC_FEATURE
<222> LOCATION: (4)..(4)
<223> OTHER INFORMATION: The functional group of the side chain is
      protected by a Boc.
<220> FEATURE:
<221> NAME/KEY: MISC_FEATURE
<222> LOCATION: (5)..(5)
<223> OTHER INFORMATION: The functional group of the side chain is
      protected by a Trt.
<220> FEATURE:
<221> NAME/KEY: MISC_FEATURE
<222> LOCATION: (7)..(9)
<223> OTHER INFORMATION: The functional group of the side chain is
      protected by a OBu.
<220> FEATURE:
<221> NAME/KEY: MISC_FEATURE
<222> LOCATION: (12)..(12)
<223> OTHER INFORMATION: The functional group of the side chain is
      protected by a Pdf.
<220> FEATURE:
<221> NAME/KEY: MISC_FEATURE
<222> LOCATION: (17)..(17)
<223> OTHER INFORMATION: The functional group of the side chain is
      protected by a Boc.
<220> FEATURE:
<221> NAME/KEY: MISC_FEATURE
<222> LOCATION: (19)..(19)
<223> OTHER INFORMATION: The functional group of the side chain is protected by a OBu.
<220> FEATURE:
<221> NAME/KEY: MISC_FEATURE
<222> LOCATION: (20)..(20)
<223> OTHER INFORMATION: The functional group of the side chain is
   protected by a Trt.
<220> FEATURE:
<221> NAME/KEY: MISC_FEATURE
<222> LOCATION: (24)..(25)
<223> OTHER INFORMATION: The functional group of the side chain is
   protected by a OBu.
<220> FEATURE:
<221> NAME/KEY: MISC_FEATURE
<222> LOCATION: (31)..(31)
<223> OTHER INFORMATION: Carboxyl group of the C-terminus is bound to
   Rink Amide MBHA. Functional group of the side chain is protected
   by a OBu.

<400> SEQUENCE: 11

Lys Asp Leu Ser Lys Gln Met Glu Glu Glu Ala Val Arg Leu Phe Ile
1               5                   10                  15

Glu Trp Leu Lys Asn Gly Gly Pro Ser Ser Gly Ala Pro Pro Pro Ser
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: The alfa-amino group of the N-terminus is
   bonded to In-DTPA via -Ahx-Bn-
<220> FEATURE:
<221> NAME/KEY: MOD_RES
<222> LOCATION: (31)..(31)
<223> OTHER INFORMATION: AMIDATION

<400> SEQUENCE: 12

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: The alfa-amino group of the N-terminus is
   protected by a Boc. The functional group of the side chain is
   protected by a OBu.
<220> FEATURE:
<221> NAME/KEY: MISC_FEATURE
<222> LOCATION: (3)..(3)
<223> OTHER INFORMATION: The functional group of the side chain is
   protected by a OBu.
<220> FEATURE:
<221> NAME/KEY: MISC_FEATURE
<222> LOCATION: (4)..(4)
<223> OTHER INFORMATION: The amino group of the side chain is bonded to
   DTPA via -Ahx-Bn-.
<220> FEATURE:
<221> NAME/KEY: MISC_FEATURE
<222> LOCATION: (5)..(5)
<223> OTHER INFORMATION: The functional group of the side chain is
   protected by a Trt.

<220> FEATURE:
<221> NAME/KEY: MISC_FEATURE
<222> LOCATION: (7)..(9)
<223> OTHER INFORMATION: The functional group of the side chain is
      protected by a OBu.
<220> FEATURE:
<221> NAME/KEY: MISC_FEATURE
<222> LOCATION: (12)..(12)
<223> OTHER INFORMATION: The functional group of the side chain is
      protected by a Pdf.
<220> FEATURE:
<221> NAME/KEY: MISC_FEATURE
<222> LOCATION: (17)..(17)
<223> OTHER INFORMATION: The functional group of the side chain is
      protected by a Boc.
<220> FEATURE:
<221> NAME/KEY: MISC_FEATURE
<222> LOCATION: (19)..(19)
<223> OTHER INFORMATION: The functional group of the side chain is
      protected by a OBu.
<220> FEATURE:
<221> NAME/KEY: MISC_FEATURE
<222> LOCATION: (20)..(20)
<223> OTHER INFORMATION: The functional group of the side chain is
      protected by a Trt.
<220> FEATURE:
<221> NAME/KEY: MISC_FEATURE
<222> LOCATION: (24)..(25)
<223> OTHER INFORMATION: The functional group of the side chain is
      protected by a OBu.
<220> FEATURE:
<221> NAME/KEY: MISC_FEATURE
<222> LOCATION: (31)..(31)
<223> OTHER INFORMATION: Carboxyl group of the C-terminus is bound to
      Rink Amide MBHA. The functional group of the side chain is
      protected by a OBu.

<400> SEQUENCE: 13

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Alfa-amino group of the N-terminus is
      protected by a Boc. The functional group of the side chain is
      protected by a OBu.
<220> FEATURE:
<221> NAME/KEY: MISC_FEATURE
<222> LOCATION: (3)..(3)
<223> OTHER INFORMATION: The functional group of the side chain is
      protected by a OBu.
<220> FEATURE:
<221> NAME/KEY: MISC_FEATURE
<222> LOCATION: (4)..(4)
<223> OTHER INFORMATION: The functional group of the side chain is
      protected by a Mmt.
<220> FEATURE:
<221> NAME/KEY: MISC_FEATURE
<222> LOCATION: (5)..(5)
<223> OTHER INFORMATION: The functional group of the side chain is
      protected by a Trt.
<220> FEATURE:
<221> NAME/KEY: MISC_FEATURE
<222> LOCATION: (7)..(9)
<223> OTHER INFORMATION: The functional group of the side chain is
      protected by a OBu.
<220> FEATURE:

```
<221> NAME/KEY: MISC_FEATURE
<222> LOCATION: (12)..(12)
<223> OTHER INFORMATION: The functional group of the side chain is
      protected by a Pdf.
<220> FEATURE:
<221> NAME/KEY: MISC_FEATURE
<222> LOCATION: (17)..(17)
<223> OTHER INFORMATION: The functional group of the side chain is
      protected by a Boc.
<220> FEATURE:
<221> NAME/KEY: MISC_FEATURE
<222> LOCATION: (19)..(19)
<223> OTHER INFORMATION: The functional group of the side chain is
      protected by a OBu.
<220> FEATURE:
<221> NAME/KEY: MISC_FEATURE
<222> LOCATION: (20)..(20)
<223> OTHER INFORMATION: The functional group of the side chain is
      protected by a Trt.
<220> FEATURE:
<221> NAME/KEY: MISC_FEATURE
<222> LOCATION: (24)..(25)
<223> OTHER INFORMATION: The functional group of the side chain is
      protected by a OBu.
<220> FEATURE:
<221> NAME/KEY: MISC_FEATURE
<222> LOCATION: (31)..(31)
<223> OTHER INFORMATION: Carboxyl group of the C-terminus is bound
      to Rink Amide MBHA. The functional group of the side chain is
      protected by a OBu.

<400> SEQUENCE: 14

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: The alfa-amino group of the N-terminus is
      protected by a Boc. The functional group of the side chain is
      protected by a OBu.
<220> FEATURE:
<221> NAME/KEY: MISC_FEATURE
<222> LOCATION: (3)..(3)
<223> OTHER INFORMATION: The functional group of the side chain is
      protected by a OBu.
<220> FEATURE:
<221> NAME/KEY: MISC_FEATURE
<222> LOCATION: (4)..(4)
<223> OTHER INFORMATION: The functional group of the side chain is
      bonded to -Ahx-Fmoc.
<220> FEATURE:
<221> NAME/KEY: MISC_FEATURE
<222> LOCATION: (5)..(5)
<223> OTHER INFORMATION: The functional group of the side chain is
      protected by a Trt.
<220> FEATURE:
<221> NAME/KEY: MISC_FEATURE
<222> LOCATION: (7)..(9)
<223> OTHER INFORMATION: The functional group of the side chain is
      protected by a OBu.
<220> FEATURE:
<221> NAME/KEY: MISC_FEATURE
<222> LOCATION: (12)..(12)
<223> OTHER INFORMATION: The functional group of the side chain is
      protected by a Pdf.
<220> FEATURE:
<221> NAME/KEY: MISC_FEATURE
```

```
<222> LOCATION: (17)..(17)
<223> OTHER INFORMATION: The functional group of the side chain is
      protected by a Boc.
<220> FEATURE:
<221> NAME/KEY: MISC_FEATURE
<222> LOCATION: (19)..(19)
<223> OTHER INFORMATION: The functional group of the side chain is
      protected by a OBu.
<220> FEATURE:
<221> NAME/KEY: MISC_FEATURE
<222> LOCATION: (20)..(20)
<223> OTHER INFORMATION: The functional group of the side chain is
      protected by a Trt.
<220> FEATURE:
<221> NAME/KEY: MISC_FEATURE
<222> LOCATION: (24)..(25)
<223> OTHER INFORMATION: The functional group of the side chain is
      protected by a OBu.
<220> FEATURE:
<221> NAME/KEY: MISC_FEATURE
<222> LOCATION: (31)..(31)
<223> OTHER INFORMATION: Carboxyl group of the C-terminus is bound to
      Rink Amide MBHA. The functional group of the side chain is
      protected by a OBu.

<400> SEQUENCE: 15

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (4)..(4)
<223> OTHER INFORMATION: The amino group of side chain is bonded to
      In-DTPA via -Ahx-Bn-.
<220> FEATURE:
<221> NAME/KEY: MOD_RES
<222> LOCATION: (31)..(31)
<223> OTHER INFORMATION: AMIDATION

<400> SEQUENCE: 16

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 17
<211> LENGTH: 39
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (12)..(12)
<223> OTHER INFORMATION: The amino group of the side chain is bonded
      to DTPA via -Ahx-Bn-.
<220> FEATURE:
<221> NAME/KEY: MOD_RES
<222> LOCATION: (39)..(39)
<223> OTHER INFORMATION: AMIDATION

<400> SEQUENCE: 17

His Gly Glu Gly Thr Phe Thr Ser Asp Leu Ser Lys Gln Met Glu Glu
1               5                   10                  15
```

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 18
<211> LENGTH: 39
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (12)..(12)
<223> OTHER INFORMATION: The amino group of the side chain is bonded
      to [111In]-DTPA via -Ahx-Bn-.
<220> FEATURE:
<221> NAME/KEY: MOD_RES
<222> LOCATION: (39)..(39)
<223> OTHER INFORMATION: AMIDATION

<400> SEQUENCE: 18

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 19
<211> LENGTH: 39
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (12)..(12)
<223> OTHER INFORMATION: Xaa is lysine

<400> SEQUENCE: 19

His Gly Glu Gly Thr Phe Thr Ser Asp Leu Ser Xaa Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (12)..(12)
<223> OTHER INFORMATION: Xaa is lysine
<220> FEATURE:
<221> NAME/KEY: MISC_FEATURE
<222> LOCATION: (12)..(12)
<223> OTHER INFORMATION: The amino group of the side chain is bonded to
      DTPA via Ahx-Bn.
<220> FEATURE:
<221> NAME/KEY: MOD_RES
<222> LOCATION: (39)..(39)
<223> OTHER INFORMATION: AMIDATION

```
<400> SEQUENCE: 20

His Gly Glu Gly Thr Phe Thr Ser Asp Leu Ser Xaa Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 21
<211> LENGTH: 39
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (12)..(12)
<223> OTHER INFORMATION: Xaa is lysine

<400> SEQUENCE: 21

His Gly Glu Gly Thr Phe Thr Ser Asp Leu Ser Xaa Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 22
<211> LENGTH: 39
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (12)..(12)
<223> OTHER INFORMATION: Xaa is lysine
<220> FEATURE:
<221> NAME/KEY: MISC_FEATURE
<222> LOCATION: (12)..(12)
<223> OTHER INFORMATION: Amino group of the side chain is bonded to
      [111In]-DTPA via Ahx-Bn.
<220> FEATURE:
<221> NAME/KEY: MOD_RES
<222> LOCATION: (39)..(39)
<223> OTHER INFORMATION: AMIDATION

<400> SEQUENCE: 22

His Gly Glu Gly Thr Phe Thr Ser Asp Leu Ser Xaa Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (12)..(12)
<223> OTHER INFORMATION: Xaa is lysine
<220> FEATURE:
<221> NAME/KEY: MISC_FEATURE
```

```
<222> LOCATION: (12)..(12)
<223> OTHER INFORMATION: The amino group of side chain is bonded to
      In-DTPA via -Ahx-Bn-.
<220> FEATURE:
<221> NAME/KEY: MOD_RES
<222> LOCATION: (39)..(39)
<223> OTHER INFORMATION: AMIDATION

<400> SEQUENCE: 23

His Gly Glu Gly Thr Phe Thr Ser Asp Leu Ser Xaa Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35
```

The invention claimed is:

1. A polypeptide having the sequence:

(Sequence ID No. 19)
His-Gly-Glu-Gly-Thr-Phe-Thr-Ser-Asp-Leu-Ser-Xaa$_{12}$-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Ser (19)

wherein:
Xaa$_{12}$ is a lysine residue in which a —Y—X group binds to an amino group in a side chain;
X is diethylenetriaminepentaacetic dianhydride (DTPA) or 1,4,7-triazacyclononnane-N,N',N"-triacetic acid (NOTA); and
Y is a linker selected from the group consisting of —CH$_2$—(C$_6$H$_4$)—, —NH—C(=S)—, —NH—(CH$_2$)$_5$—C(=O)—, and combination thereof.

2. A polypeptide having the sequence:

(Sequence ID No. 21)
His-Gly-Glu-Gly-Thr-Phe-Thr-Ser-Asp-Leu-Ser-Xaa$_{12}$-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Ser (21)

wherein:
Xaa$_{12}$ is a lysine residue in which a —Y—X' group binds to an amino group in a side chain;
X' is a chelating site and a radioactive metal nuclide chelated by the chelating site, where the chelating site is diethylenetriaminepentaacetic dianhydride (DTPA) or 1,4,7-triazacyclononnane-N,N',N"-triacetic acid (NOTA); and
Y is a linker selected from the group consisting of —CH$_2$—(C$_6$H$_4$)—, —NH—C(=S)—, —NH—(CH$_2$)$_5$—C(=O)—, and combination thereof.

3. A composition comprising the polypeptide according to claim 2 and a pharmaceutical carrier.

4. A kit comprising:
the polypeptide according to claim 1 and
a radioactive metal nuclide.

5. The polypeptide according to claim 1, wherein Y is —CH$_2$—(C$_6$H$_4$)—NH—C(=S)—NH—(CH$_2$)$_5$—C(=O)—.

6. The polypeptide according to claim 1, wherein X is DTPA, and Y is —CH$_2$—(C$_6$H$_4$)—NH—C(=S)—NH—(CH$_2$)$_5$—C(=O)—.

7. The polypeptide according to claim 2, wherein the radioactive metal nuclide is $^{111}$In.

8. The polypeptide according to claim 2, wherein Y is —CH$_2$—(C$_6$H$_4$)—NH—C(=S)—NH—(CH$_2$)$_5$—C(=O)—.

9. The polypeptide according to claim 2, wherein X' is $^{111}$In-DTPA, and Y is —CH$_2$—(C$_6$H$_4$)—NH—C(=S)—NH—(CH$_2$)$_5$—C(=O)—.

10. A method for imaging pancreatic islet cells, comprising:
administering to a subject the polypeptide according to claim 2 in an effective amount to provide detectable images of pancreatic islet cells;
detecting radioactive signals of the polypeptide emitted from the pancreatic islet cells;
reconstructing the detected signals;
converting the signals to images; and
displaying the images of the pancreatic islet cells.

* * * * *